United States Patent [19]
Bucholz

[11] Patent Number: 5,851,183
[45] Date of Patent: *Dec. 22, 1998

[54] SYSTEM FOR INDICATING THE POSITION OF A SURGICAL PROBE WITHIN A HEAD ON AN IMAGE OF THE HEAD

[75] Inventor: Richard D. Bucholz, St. Louis, Mo.

[73] Assignee: St. Louis University, St. Louis, Mo.

[ * ] Notice: This patent issued on a continued prosecution application filed under 37 CFR 1.53(d), and is subject to the twenty year patent term provisions of 35 U.S.C. 154(a)(2).

[21] Appl. No.: 543,516

[22] Filed: Oct. 16, 1995

Related U.S. Application Data

[63] Continuation of Ser. No. 858,980, May 15, 1992, abandoned, which is a continuation-in-part of Ser. No. 600,753, Oct. 19, 1990, abandoned.

[51] Int. Cl.$^6$ ........................................................ A61B 6/00
[52] U.S. Cl. ........................... 600/425; 600/424; 600/429; 600/443; 600/439; 606/130
[58] Field of Search ............................... 128/653.1, 653.2, 128/653.5; 606/130; 364/413.9, 413.22; 600/424, 425, 437, 426, 429, 407, 443, 439

[56] References Cited

U.S. PATENT DOCUMENTS

D. 291,246  8/1987  Lower .
D. 349,573  8/1994  Bookwalter .

(List continued on next page.)

FOREIGN PATENT DOCUMENTS 0018166   4/1980   European Pat. Off. .
0062941   10/1982  European Pat. Off. .
0 155 857  1/1985   European Pat. Off. .
0 207 452  1/1987   European Pat. Off. .
0326768   12/1988  European Pat. Off. .

(List continued on next page.)

OTHER PUBLICATIONS

Reinhardt et al, "A Computer Assisted Device for the Intra Operative CT–Correlated Localization of Brain Tumors," Eur. Surg. Res. 20:52–58 (1988).

Friets et al., "A Frameless Stereotaxic Operating Microscope for Neurosurgery," IEEE Transactions on Biomedical Engineering 36, No. 6 (Jun. 1989), pp. 608, 613–617.

Roberts et al., "A Frameless Stereotaxic Integration of Computerized Tomographic Imaging and the Operating Microscope" J. Neurosurg 65: 545–549 (1986), pp. 545–549.

"SACDAC User's Guide, Version 2e" (Mar. 1989) by PixSys, Inc., pp. 0–1 thru 5–3.

"Offset Probe for Science Accessories' GP–8–3d digitizer" (Dec. 1987) by PixSys, Inc., one page.

(List continued on next page.)

Primary Examiner—Ruth S. Smith
Attorney, Agent, or Firm—Finnegan, Henderson, Farabow, Garrett & Dunner, L.L.P.

[57] ABSTRACT

A system for determining a position of a probe (302) relative to an object such as a head (390) of a body of a patient. The head includes a surface such as a forehead (394) having a contour. The head is placed in a cradle (392) equipped with an arc (393). The cross sectional images of the head are determined relative to the arc. A hand held unit (380) optically scans the forehead and the arc. During scanning to generate the cross sectional images, the optical scanner (380) is used to determine the position of the forehead (394) relative to the cradle (392). During surgery, the optical scanner (380) also determines the position of the forehead (394) relative to a base ring (306). An array (300) for receiving radiation emitted from the probe (302) and from the base ring (306) generates signals indicating the position of the tip of the probe (302) relative to the base ring (306). A stereotactic imaging system selects and displays the image of the head closest to the measured position of the tip of the probe (302).

14 Claims, 9 Drawing Sheets

U.S. PATENT DOCUMENTS

| | | |
|---|---|---|
| D. 353,668 | 12/1994 | Banks . |
| D. 357,534 | 4/1995 | Hayes . |
| D. 359,557 | 6/1995 | Hayes . |
| 3,821,469 | 6/1974 | Whetstone et al. ............... 178/18 |
| 3,868,565 | 2/1975 | Kuipers . |
| 3,963,028 | 6/1976 | Cooley et al. . |
| 3,983,474 | 9/1976 | Kuipers ........................ 324/43 R |
| 4,058,114 | 11/1977 | Soldner . |
| 4,068,156 | 1/1978 | Johnson et al. . |
| 4,117,337 | 9/1978 | Staats . |
| 4,182,312 | 1/1980 | Mushabac ........................ 433/68 |
| 4,209,254 | 6/1980 | Reymond . |
| 4,259,725 | 3/1981 | Andrews et al. ............ 364/413.22 |
| 4,262,306 | 4/1981 | Renner . |
| 4,341,220 | 7/1982 | Perry ............................... 128/630 |
| 4,358,856 | 11/1982 | Stivender et al. . |
| 4,368,556 | 1/1983 | Wanner et al. . |
| 4,396,945 | 8/1983 | DiMatteo et al. . |
| 4,398,540 | 8/1983 | Takemura et al. ........... 128/660.05 |
| 4,407,298 | 10/1983 | Lentz et al. . |
| 4,419,012 | 12/1983 | Stephenson . |
| 4,457,311 | 7/1984 | Sorenson et al. . |
| 4,465,069 | 8/1984 | Barbier et al. .................. 128/303 B |
| 4,473,074 | 9/1984 | Vassiliadis . |
| 4,506,676 | 3/1985 | Duska ............................ 128/653 |
| 4,543,959 | 10/1985 | Sepponen .................... 128/660.04 |
| 4,571,834 | 2/1986 | Fraiser et al. . |
| 4,583,538 | 4/1986 | Onik et al. .................... 128/303 B |
| 4,585,350 | 4/1986 | Pryer et al. . |
| 4,592,352 | 6/1986 | Patil . |
| 4,602,622 | 7/1986 | Bar et al. . |
| 4,608,977 | 9/1986 | Brown ........................... 128/303 B |
| 4,638,798 | 1/1987 | Sheldon et al. ............... 128/303 B |
| 4,649,504 | 3/1987 | Krouglicof et al. . |
| 4,651,732 | 3/1987 | Frederick . |
| 4,659,971 | 4/1987 | Suzuki et al. . |
| 4,660,970 | 4/1987 | Ferrano ............................... 356/1 |
| 4,672,306 | 6/1987 | Thong . |
| 4,673,352 | 6/1987 | Hansen . |
| 4,674,057 | 6/1987 | Caughman et al. . |
| 4,686,997 | 8/1987 | Oloff et al. . |
| 4,698,777 | 10/1987 | Toyoda et al. . |
| 4,701,047 | 10/1987 | Eibert et al. . |
| 4,701,049 | 10/1987 | Beckmann et al. .................. 356/1 |
| 4,701,407 | 10/1987 | Seppel ................................ 435/1 |
| 4,705,395 | 11/1987 | Hageniers et al. .................. 356/1 |
| 4,705,401 | 11/1987 | Addleman et al. ................ 356/376 |
| 4,706,665 | 11/1987 | Gouda . |
| 4,709,156 | 11/1987 | Murphy et al. .................. 250/560 |
| 4,721,384 | 1/1988 | Dietrich et al. . |
| 4,721,388 | 1/1988 | Takagi et al. . |
| 4,722,056 | 1/1988 | Roberts et al. . |
| 4,723,544 | 2/1988 | Moore et al. . |
| 4,727,565 | 2/1988 | Ericson . |
| 4,733,661 | 3/1988 | Palestrant . |
| 4,733,662 | 3/1988 | DeSatnick . |
| 4,733,969 | 3/1988 | Case et al. ...................... 356/375 |
| 4,737,032 | 4/1988 | Addleman et al. ................ 356/376 |
| 4,743,770 | 5/1988 | Lee .................................. 250/560 |
| 4,743,771 | 5/1988 | Sacks et al. .................... 250/560 |
| 4,745,290 | 5/1988 | Frankel et al. ................. 250/560 |
| 4,750,487 | 6/1988 | Zanetti . |
| 4,753,528 | 6/1988 | Hines et al. ........................ 356/1 |
| 4,757,921 | 4/1988 | Goldwasser et al. . |
| 4,761,072 | 8/1988 | Pryor .................................. 356/1 |
| 4,762,016 | 8/1988 | Stoughton et al. . |
| 4,764,015 | 8/1988 | Bieringer et al. . |
| 4,764,016 | 8/1988 | Johanasson ....................... 356/371 |
| 4,767,934 | 8/1988 | Stauffer . |
| 4,771,787 | 9/1988 | Wurster et al. ............... 128/660.03 |
| 4,775,235 | 10/1988 | Hecker et al. . |
| 4,776,749 | 10/1988 | Wanzenberg et al. . |
| 4,779,212 | 10/1988 | Levy ................................ 364/562 |
| 4,782,239 | 11/1988 | Hirose et al. ................... 250/561 |
| 4,791,934 | 12/1988 | Brunnett ........................... 128/653 |
| 4,793,355 | 12/1988 | Crum et al. . |
| 4,794,262 | 12/1988 | Sato et al. ....................... 250/560 |
| 4,803,645 | 2/1989 | Ohtomo et al. . |
| 4,805,615 | 2/1989 | Carol . |
| 4,809,694 | 3/1989 | Ferrara . |
| 4,821,200 | 4/1989 | Oberg ........................... 364/474.24 |
| 4,821,206 | 4/1989 | Arora . |
| 4,822,163 | 4/1989 | Schmidt ............................... 356/1 |
| 4,825,091 | 4/1989 | Brever et al. ................... 250/560 |
| 4,829,373 | 5/1989 | Leberl et al. ....................... 358/88 |
| 4,835,710 | 5/1989 | Schnelle et al. . |
| 4,836,778 | 6/1989 | Baumrind et al. ................. 433/69 |
| 4,837,669 | 6/1989 | Tharp et al. . |
| 4,841,967 | 6/1989 | Chang et al. . |
| 4,875,478 | 10/1989 | Chen . |
| 4,896,673 | 1/1990 | Rose et al. . |
| 4,931,056 | 6/1990 | Ghajar et al. ...................... 606/130 |
| 4,933,843 | 6/1990 | Scheller et al. . |
| 4,943,296 | 7/1990 | Funakubo et al. . |
| 4,945,914 | 8/1990 | Allen ............................. 128/653 R |
| 4,955,891 | 9/1990 | Carol . |
| 4,961,422 | 10/1990 | Marchosky . |
| 4,982,188 | 1/1991 | Fodale et al. . |
| 4,991,579 | 2/1991 | Allen ............................. 128/653 R |
| 5,005,142 | 4/1991 | Lipchak et al. . |
| 5,016,639 | 5/1991 | Allen ............................. 128/653 R |
| 5,017,139 | 5/1991 | Mushabac ........................ 433/109 |
| 5,027,818 | 7/1991 | Bova et al. ..................... 128/653.1 |
| 5,039,867 | 8/1991 | Nishihara et al. . |
| 5,047,036 | 9/1991 | Koutrouvelis . |
| 5,050,608 | 9/1991 | Watanabe et al. ............ 128/653.1 |
| 5,059,789 | 10/1991 | Salcudean et al. . |
| 5,078,140 | 1/1992 | Kwoh .............................. 128/653.1 |
| 5,078,142 | 1/1992 | Siczek et al. . |
| 5,079,699 | 1/1992 | Tuy et al. . |
| 5,080,662 | 1/1992 | Paul . |
| 5,094,241 | 3/1992 | Allen ............................. 128/653.1 |
| 5,097,839 | 3/1992 | Allen ............................. 128/653.1 |
| 5,099,846 | 3/1992 | Hardy ........................... 606/130 X |
| 5,107,839 | 4/1992 | Houdek et al. ............... 606/130 X |
| 5,119,817 | 6/1992 | Allen ............................. 128/653.1 |
| 5,142,930 | 9/1992 | Allen et al. ........................ 74/469 |
| 5,178,164 | 1/1993 | Allen ................................. 128/898 |
| 5,186,174 | 2/1993 | Schlöndorff et al. ............. 128/653.1 |
| 5,193,106 | 3/1993 | DeSena ............................ 378/163 |
| 5,197,476 | 3/1993 | Nowacki et al. ............ 128/660.03 |
| 5,198,877 | 3/1993 | Schulz . |
| 5,207,223 | 5/1993 | Adler ............................ 128/653.1 |
| 5,211,164 | 5/1993 | Allen ............................ 128/653.1 |
| 5,222,499 | 6/1993 | Allen et al. . |
| 5,224,049 | 6/1993 | Mushabac ..................... 364/474.05 |
| 5,230,338 | 7/1993 | Allen et al. .................. 606/130 X |
| 5,249,581 | 10/1993 | Horbal et al. . |
| 5,251,127 | 10/1993 | Raab .............................. 606/130 X |
| 5,257,998 | 11/1993 | Ota et al. . |
| 5,261,404 | 11/1993 | Mick et al. . |
| 5,279,309 | 1/1994 | Taylor et al. . |
| 5,291,889 | 3/1994 | Kenet et al. . |
| 5,295,200 | 3/1994 | Boyer . |
| 5,295,483 | 3/1994 | Nowacki et al. . |
| 5,299,288 | 3/1994 | Glassman et al. . |
| 5,305,091 | 4/1994 | Gelbart et al. . |
| 5,305,203 | 4/1994 | Raab ............................ 364/413.13 |
| 5,355,129 | 10/1994 | Baumann . |
| 5,383,454 | 1/1995 | Bucholz . |
| 5,494,034 | 2/1996 | Schlondorff et al. . |
| 5,531,520 | 7/1996 | Grimson et al. . |

| | | |
|---|---|---|
| 5,622,170 | 4/1997 | Schulz . |
| 5,638,819 | 6/1997 | Manwaring et al. . |
| 5,662,111 | 9/1997 | Cosman . |
| 5,682,886 | 11/1997 | Delp et al. . |
| B1 5,383,454 | 12/1996 | Bucholz . |

FOREIGN PATENT DOCUMENTS

| | | |
|---|---|---|
| 0 322 363 | 6/1989 | European Pat. Off. . |
| 0427358 | 10/1990 | European Pat. Off. . |
| 0456103 | 5/1991 | European Pat. Off. . |
| 0359773 | 10/1993 | European Pat. Off. . |
| 2 417 970 | 10/1979 | France . |
| DE2534516A1 | 2/1976 | Germany . |
| DE2852949A | 6/1980 | Germany . |
| DE3205085A1 | 9/1982 | Germany . |
| 3508730 | 9/1986 | Germany . |
| G 87 01 668.0 | 2/1987 | Germany . |
| DE8701668 | 5/1987 | Germany . |
| 3205915 | 9/1993 | Germany . |
| 62-000327 | 1/1987 | Japan . |
| 2094590 | 2/1982 | United Kingdom . |
| 2094590 | 9/1982 | United Kingdom ................ 128/653.1 |
| WO88/09151 | 12/1988 | WIPO . |
| WO 90/05494 | 5/1990 | WIPO . |
| WO90/05494 | 5/1990 | WIPO . |
| WO 91/04711 | 4/1991 | WIPO . |
| WO 91/07726 | 5/1991 | WIPO . |
| WO91/07726 | 5/1991 | WIPO . |
| WO92/00702 | 12/1992 | WIPO . |

OTHER PUBLICATIONS

"Alignment Procedure for the PixSys Two–Emitter Offset Probe for the SAC GP–8–3d Sonic Digitizer" (undated) by PixSys, Inc., 3 unnumbered pages.

"PixSys: 3–D Digitizing Accessories" (Aug. 1989) by PixSys, Inc., 6 unnumbered pages.

"Design Aide" (Mar. 1989) by PixSys, Inc., 5 unnumbered pages.

"3–D Digitizer Captures the World" (Oct. 1990) BYTE Magazine, p. 43.

An Articulated Neurosurgical Navigation System Using MRI and CT Images (Feb., 1988) by Yukio Yosugi et al., pp. 147–152.

A New Imaging Method for Intraoperative Therapy Control in Skull–Base Surgery (1988) by Ralph Mosges et al., pp. 245–246.

A Frameless Stereotaxic Integration of Computerized Tomographic Imaging and the Operating Microscope (Oct., 1986) by David W. Roberts, M.D. et al., pp. 545–549.

Computed Tomography–Guided Sterotactic Systems (1983) by M. Peter Heilbrun, M.D., pp. 564–581.

Computed Tomography–Directed Stereotaxy for Biopsy and Interstitial Irradiation of Brain Tumors; Technical Note (1982) by Alexander R. MacKay, M.D. et al., pp. 38–42.

Computed Tomographic Guidance Streotaxis in the Management of Intracranial Mass Lesions (1983) by M.L.J. Apuzzo et al., pp. 277–285.

A Comparison of CT–Steretotaxic Brain Biopsy Techniques (1984) by Neil B. Horner, M.D. et al., pp. 367–373.

Computed Tomography Plane of the Target Approach in Computed Tomographic Stereotaxis (1984) by Arun–Angelo Patil, M.D. pp. 410–414.

Trigeminus Stereoguide: An Instrument for Stereotactic Approach Through the Foramen Ovale and Foramen Jugulare (1984) by Lauri V. Laitinen, M.D., pp. 519–523.

CT–Guided Stereotactic Biopsies Using a Modified Frame and Gildenberg Techniques (1984) by D.E. Bullard et al., pp. 590–595.

A Multipurpose CT–Guided Stereotactic Instrument of Simple Design (1983) by J.M. Van Buren et al., pp. 211–216.

Computer–Assisted Stereotaxic Laser Resection of Intra–Axial Brain Neoplasms (Mar. 1986) by patrick J. Kelly, M.D. et al pp. 427–439.

Three–Dimensional Digitizer (Neuronavigator): New Equipment for computed Tomography–Guided Stereotaxic Surgery (1987) by Eiju Watanabe, M.D. et al., pp. 543–547.

Watanabe et al, "Three Dimensional Digitizer (Neuronavigator) New Equipment for Computed Tomography–Guided Stereotaxic Surgery," 27 Surg. Neurol. 543–7 (1987).

Reinhardt et al., "Interactive Sonar–Operated Device for Stereotactic and Open Surgery," Stereotac Funct Neurosurg 1990; 54&55:393–397.

Krybus et al., "Navigation Support for Surgery by Means of Optical Position Detection," Lehrstuhl für Meβtechnik.

Watanabe, "Neuronaigator," Igaku–no–Ayumi, vol. 137, No., 6 May 10, 1986 (With Translation).

Adams et al., "Aide Au Reperage Tridimensionnel Pour La Chirurgie De La Base Du Crane," Innov. Tech. Biol. Med., vol. 13, No. 4, pp. 409–424, 1992.

Reinhardt, "Neuronavigation: A Ten–Year Review," Neurosurgery, vol. 23, pp. 329–341, 1992.

Klimek, "Long–Term Experience with Different Types of Localization Systems in Skull–Base Surgery," Ear, Nose, and Surgery, vol. 51, pp.635–638, 1993.

Mazier, et al., "Computer Assisted Interventionist Imaging: Application to the Vertebral Column Surgery," IEEE, vol. 12, No. 1, 1990.

Lavallee, "A New System for Computer Assisted Neurosurgery," IEEE, 1989.

Sautot, et al., "Computer Assisted Spine Surgery: a First Step Toward Clinical Application in Orthopaedics," IEEE, 1992.

Reinhardt et al., "CT–Guided 'Real Time' Stereotaxy," Acta Neurochirurgica Suppl. 46, 107–108, 1989.

Reinhardt, "Surgery of Brain Neoplasms Using 32–P Tumour Marker," Acta Neurochir 97; 89–94, 1989.

Reinhardt et al., "Sonic Stereometry in Microsurgical Procedures for Deep–Seated Brain Tumors and Vascular Malformations," Neurosurgery, vol. 32, No. 1, Jan. 1993.

Jacques, et al., "A Computerized Microstereotactic Method to Approach, 3–Dimensionally Reconstruct, Remove and Adjuvantly Treat Small CNS Lesions," Appl. Neurophysiol. 43: 176–182, 1980.

Reinhardt et al., "Mikrochirurgische Entfernung tiefliegender Gefaβmiβbildungen mit Hilfe der Sonar–Stereometrie," Ultra–schall in Med. 12, 80–84, 1991.

Adams, et al., "Computer–Assisted Surgery," Medical Imaging, IEEE, pp. 43–51, May 1990.

Pelizzari, "Interactie 3D Patient–Image Registration" Information Procession in Medical Imaging, Proceedings, (Jul., 1991), pp. 132–141.

Kato, et al., "A Frameless, Armless Navigational System for Computer–Assisted Neurosurgery," Journal of Neurosurg. vol. 74, pp. 845–849, May 1991.

Reinhardt et al., "A Computer–Assisted Device for the Intraoperative CT–Correlated Localization of Brain Tumors," Eur. surg. Res. 20: 51–58, pp. 51–58, 1988.

Cinquin et al., "Computer Assisted Medical Interventions," IARP, pp. 63–65, Sep. 1989.

Mazier et al., "Chirurgie De La Colonne Vertebrale Assistee Par Ordinateur: Application Au Vissage Pediculaire," Innov. Tech. Biol. Med.; vol. 11, No. 5, pp. 559–566, 1990.

Lavallee et al., "Computer Assisted Driving of a Needle into the Brain," CAR, pp. 416–420, 1989.

Cinquin, et al., "IGOR: Image Guided Robot. Methodology, Applications," IEEE EMBS, 1992.

Champleboux, et al., "Accurate Calibration of Cameras and Range Imaging Sensors: the NPBS Method," IEEE 1992.

Lavallee, et al., "Computer Assisted Interventionist Imaging: The Instance of Stereotactic Brain Surgery," Medinfo, 1989.

Lavallee, "Vi Adaptation De La Methodologie A Quelques Applicatiosn Cliniques," Methodologie des GMCAO.

Lavallee, et al., "Computer Assisted Puncture," Afcet, pp. 439–449, Nov. 1987.

Paul, et al., "Development of a Surgical Robot for Cementless Total Hip Arthroplasty," Clinical Orthopaedics, No. 285 pp. 57–66, Dec. 1992.

Lavallee et al., "Computer Assisted Medical Interentions," NATO ASI Series, vol. F60, p. 302312, 1990.

Lavallee, et al., "Matching of Medical Images for Computed and Robot Assisted Surgery," 1991.

Champleboux, "Utilisation De Fonctions Splines Pour La Mise Au Point d'Un Capteur Tridimensionnel Sans Contact," Jul. 1991.

Russell A. Brown, "A Stereotactic Head Frame for Use with CT Body Scanners," *Inv. Radiol.*, vol. 14, No. 4, pp. 300–304, Jul. 1979.

Ludwig Adams et al., "Medical Imaging: Computer-Assisted Surgery," *IEEE Computer Graphics and Applications*, pp. 43–51, May 1990.

Eric E. Awwad et al., "MR Imaging of Lumbar Juxtaarticular Cysts," *Journal of computer Assisted Tomography*, vol. 14 No. 3, pp. 415–417, May/Jun. 1990.

Eric E. Awwad et al., "Post–Traumatic Spinal Synovial Cyst with Spondylolysis CT Features," *Journal of Computer Assisted Tomography*, vol. 13, No.2, pp. 334–337, Mar./Apr. 1989.

Gayle Hanson, "Robots Roll into Operating Rooms," *Insight*, Apr. 8, 1991, pp. 44–45.

P.J. Kelly, et al., "Precision Resection of Intra–Axial CNS Lesions by CT–Based Stereotactic Craniotomy and Computer Monitored $CO_2$ Laser," *Acta Neurochirurgica*, Springer–Verlag 1983, vol. 68, 1983, pp. 1–9.

Bill Dever and S. James Zinreich, M.D., "OR role seen for 3–D imaging," *Radiology Today*, 2 pages, Feb. 1991.

Edmund M. Glaser et al., "The Image–Combining Computer Microscope–an Interactive Instrument for Morphometry of the Nerous System," *Journal of Neuroscience Methods*, vol. 8, pp. 17–32, 1983.

Camilo R. Gomez et al., "Transcranial Doppler Ultrasound Following Closed Head Injury: Vasospasm or Vasoparalysis?," *Surg. Neurol.*, vol. 35, No. 1, pp. 30–35, Jan. 1991.

J.F. Hatch et al., "Reference–Display System for the Integration of CT Scanning and the Operating Microscope," Proceedings of the Eleventh Annual Northeast Bioengineering Conference, pp. 252–254, Mar. 15, 1985.

M. Peter Heilburn et al., "Preliminary Experience with a Brown–roberts–Wells (BRW) Computerized Tomography Stereotaxic Guidance system," *J. Neurosurg.*, vol. 59, pp. 217–222, Aug. 1983.

C.A. Pelizzari et al., "Interactive 3D Patient–Image Registration" *Information Procession in Medical Imaging, Proceedings*, pp. 132–141, Jul. 1991.

Richard D. Penn et al., "Stereotactic Surgery with Image Processing of Computerized Tomographics Scans," *Neurosurgery*, vol. 3, No. 2, pp. 157–163, May 26, 1978.

Claude Picard et al., "The First Human Stereotaxic Apparatus" *J. Neurosurg.*, vol. 59, pp. 673–676, Oct. 1983.

Mazier et al., "Computer Assisted Vertebral Column Surgery: Application to the Spinal Pedicle Fixation," Innov. Tech. Biol. Med., vol. 11/5, 1990, p.

Patrick J. Kelly, M..D., et al. "A Microstereotactic Approach to Deep–seated Arteriovenous Malformations," *Surgical Neurology*, vol. 17, No. 4, Apr. 1982, pp. 260–262.

S. Lavalee, et al., "Matching 3–D Smooth Surfaces with their 2–d Projections using 3–D Distance Maps," SPIE, vol. 1570, 1991, pp. 322–336.

Y.C. Shiu, et al., "Finding the Mounting Position of a Sensor by Solving a Homogeneous Transform Equation of Form AX=XB," IEEE , 1987, pp.1666–1671.

K.S. Arun et al., "Transactions on Pattern Analysis and Machine Intelligence," IEEE , vol. PAMI–9, No. 5, 1987, pp. 698–770.

F. Mesqui et al., "Real–Time, Noninvasive Recording and Three–Dimensional Display of the functional Movements of an Arbitrary Mandible Point," *SPIE Biostereometrics '85*, vol. 602, pp. 77–84, Dec. 3–6, 1985.

Kurt R. Smith et al., "Multimodality Image Analysis and Display Methods for Improved Tumor Localization in Stereotactic Neurosurgery," *Annual Conference of the IEEE Engineering in Medicine and Biology Society*, vol. 13, No. 1, p. 0210, 1991.

B. Leonard Holman, et al., Computer–Assisted Superimposition of Magnetic Resonance and High–Resolution Technetium–99–m–HMPAO and Thallium–201 SPECT Images of the Brain, *The Journal of Nuclear Medicine*, vol. 32, No. 8, Aug. 1991, pp. 1478–1484.

C.A. Pelizzari, et al., 3D Patient/Image Registration: Application to Radiation Treatment Planning, *Medical Physics*, vol. 18, No. 3, May/Jun. 1991, p. 612.

D.J. Valentino, et al., Three–Dimensional Visualization of Human Brain Structure–Function Relationships, *The Journal of Nuclear Medicine*, Oct. 1989, Posterboard 1136, vol. 30, No. 10, p. 1747.

David N. Levin, et al., "The Brain: Integrated Three–dimensional Display of MR and PET Images," *Radiology*, Sep. 1989, vol. 172, No. 3, pp. 783–789.

Charles A. Pelizzari, et al., "Accurate Three–Dimensional Registration of CT, PET and/or MR Images of the Brain," *Journal of Computer Assisted Tomography*, 13(1):20–26, Jan./Feb. 1989, Raven Press, pp. 20–26.

C.A. Pelizzari, et al., "Interactie 3D Patient–Image Registration," *Lecture Notes in Computer Science*, Springer–Verlag, Wye, UK, 1991 Proceedings, pp. 132–141.

D. Levin, et al., "Multimodality 3–D View of the Brain Created from MRI and PET Scans," *SMRI 1989: Seventh Annual Meeting Program and Abstracts*, vol. 7, Supplement 1, p. 89.

C.A. Pelizzari, et al., "Three Dimensional Correlation of PET, CT and MRI Images," *The Journal of Nuclear Medicine, Abstract Book*, 34th Annual Meeting, Toronto, Canada, 1987, vol. 28, No. 4, Poster Session No. 528, p. 682.

John F. Hatch, "Reference–Display System for the Integration of CT Scanning and the Operating Microscope," Trustees of Dartmouth College, Oct. 1984, entire thesis.

Patrick J. Kelly, M.D., et al., "A Stereotactic Approach to Deep–Seated Central Nervous System Neoplasms Using the Carbon Dioxide Laser," *Surgical Neurology*, vol. 15, No. 5, May 1981, pp. 331–334.

Patrick J. Kelly, et al., "Stereotactic CT Scanning for the Biopsy of Intracranial Lesions and Functional Neurosurgery," *Applied Neurophysiology*, Dec. 1983, Karger, AG, Basel, pp. 193–199.

C. Hunter Shelden, M.D., et al., "Development of a computerized microstereotaxic method for localization and removal of minute CNS lesions under direct 3–D vision," *J. Neurosurg*, vol. 52, Jan. 1980, pp. 21–27.

Skip Jacques, M.D., et al., "Computerized three–dimensional sterotaxic removal of small central nervous system lesions in patients," *J. Neurosurg*, vol. 53, No. 6, Dec. 1980, pp. 816–820.

Afshar, Farhad, et al., "A three–dimensional reconstruction of the human brain stem," *J. Neurosurg.*, vol. 57, Oct. 1982, pp. 491–495.

Bajcsy, Ruzena, et al., "Computerized Anatomy Atlas of the Human Brain," Proceedings of the Second Annual Conference & Exhibition of The National Computer Graphics Association, Inc., Jun. 14–18, 1981, pp. 435–441.

Batnitzky, Solomon, M.D., et al., "Three–Dimensional Computer Reconstructions of Brain Lesions from Surface Contours Provided by Computed Tomography: A Prospectus," *Neurosurgery*, vol. 11, No. 1, 1982, pp. 73–84.

Bergström, Mats, et al., "Stereotaxic Computed Tomography," *Am. J. Roentgenol*, 127:167–170, 1976, pp. 167–170.

Birg, W., et al., "A Computer Programme System for Stereotactic Neurosurgery," *Acta Neurochirurgica Suppl.*, 24, 1977, 99–108.

Boëthius, J., et al., "Stereotactic Biopsies and Computer Tomography in Gliomas," *Acta Neurochirurgica*, vol. 40, Fasc. 3–4, 1978, pp. 223–232.

Boëthius, J., et al., "Stereotaxic computerized tomography with a GE 8800 scanner," *J. Neurosurg*, vol. 52, 1980, pp. 794–800.

Brown, Russell A., M.D., "A computerized tomography–computer graphics approach to stereotaxic localization," *J. Neurosurg*, vol. 50, 1979, pp. 715–720.

Gildenberg, Philip L., M.D., et al., "Calculation of Stereotactic Coordinates from the Computed Tomographic Scan," *Neurosurgery*, vol. 10, No. 5, 1982, pp. 580–586.

Gleason, Curtis A., Ph.D., et al., "Stereotactic Localization (with Computerized Tomographic Scanning), Biopsy, and Radiofrequency Treatment of Deep Brain Lesions," *Neurosurgery*, vol. 2, No. 3, 1978, pp. 217–222.

Gouda, Kasim I., M.D., et al., "New frame for stereotaxic surgery," *J. Neurosurg*, vol. 53, 1980, pp. 256–259.

Greitz, T., et al., "Head Fixation System for Integration of Radiodiagnostic and Therapeutic Procedures," *Neuroradiology*, vol. 19, No. 1, 1980, pp. 1–6.

Hahn, Joseph F., M.D., et al., "Needle Biopsy of Intracranial Lesions Guided by Computerized Tomography," *Neurosurgery*, vol. 5, No. 1, 1979, pp. 11–15.

Hinck, Vincent C., M.D., et al., "A precise technique for craniotomy localization using computerized tomography," *J. Neurosurg*, vol. 54, Mar. 1981, pp. 416–418.

Hoerenz, Peter, "The Operating Microscope, I., Optical Principles, Illumination Systems, and Support Systems," *Journal of Microsurgery*, vol. 1, Mar.–Apr. 1980, pp. 364–369.

Hounsfield, G.N., Computerized transverse axial scanning (tomography): Part 1., Description of System, *British Journal of Radiology*, vol. 46, 1973, pp. 1016–1022.

Kaufman, Howard H., M.D., "New Head–positioning System for Use with Computed Tomographic Scanning," *Neurosurgery*, vol. 7, No. 2, 1980, pp. 147–149.

Leksell, L., et al., "Stereotaxis and Tomography, A Technical Note," *Acta Neurochirurgica*, vol. 52, Fasc–12, 1980, pp. 1–7.

Levinthal, Robert, M.D., et al., "Technique for Accurate Localization with the CT Scanner," *Bulletin of the Los Angeles Neurological Societies*, vol. 41, No. 1, Jan. 1976, pp. 6–8.

Lunsford, L. Dade, M.D., "Innovations in Stereotactic Technique Coupled with Computerized Tomography," *Contemporary Neurosurgery*, 1982, pp. 1–6.

MacKay, Alexander R., M.D., et al., "Computed Tomography–directed Sterotaxy for Biopsy and Interstitial Irradiation of Brain Tumors: Technical Note," *Neurosurgery*, vol. 11, No. 1, Jul. 1982, pp. 38–42.

Maroon, Joseph C., M.D., et al., "Intracranial biopsy assisted by computerized tomography," *J. Neurosurg.*, vol. 46, No. 6, Jun. 1977, pp. 740–744.

Moran, Christopher J., M.D., et al., "Central Nervous System Lesions Biopsied or Treated by CT–Guided Needle Placement," *Radiology*, vol. 131, No. 3, Jun. 1979, pp. 681–686.

Mundinger, F., et al., "Computer–Assisted Sterotactic Brain Operations by Means Including Computerized Axial Tomography," *Applied Neurophysiology*, vol. 41, Nos. 1–4, 1978, pp. 169–182.

Mundinger, F., et al., "Treatment of Small Cerebral Gliomas with CT–Aided Stereotaxic Curietherapy," *Neuroradiology*, vol. 16, Jun. 4–10, 1978, pp. 564–567.

Norman, David, M.D., et al., "Localization with the EMI Scanner, " *The American Journal of Roentgenology Radium Therapy and Nuclear Medicine,*vol. 125, No. 125, No. 4, Dec. 1975, pp. 961–964.

O'Leary, Daniel H., M.D., et al., "Localization of vertex lesions seen on CT scan," *J. Neurosurg*, vol. 49, No. 1, Jul. 1978, pp. 71–74.

Perry, John H., Ph.D., et al., "Computed Tomography–guided Stereotactic Surgery: Conception and Development of a New Stereotactic Methodology," *Neurosurgery*, vol. 7, No. 4, Oct. 1980, pp. 376–381.

Piskun, Walter S., Major, et al., "A Simplified Method of CT Assisted Localization and Biopsy of Intracranial Lesions," *Surgical Neurology*, vol. II, Jan.–Jun. 1979, pp. 413–417.

Rosenbaum, Arthur E., et al., "Computerized Tomography Guided Stereotaxis: A New Approach," *Applied Neurophysiology*, vol. 43, Nos. 3–5, Jun. 4–7, 1980. pp. 172–173.

Scarabin, J.M., et al., "Stereotaxic Exploration in 200 Supratentorial Brain Tumors," *Neuroradiology*, vol. 16, Jun. 4–10, 1978, pp. 591–593.

Yeates, Andrew, M.D., et al., "Simplified and accurate CT–guided needle biopsy of central nervous system lesions," *Journal of Neurosurgery*, vol. 57, No. 3, Sep. 1982, pp. 390–393.

Castleman, Kenneth R., "Digital Image Processing," Prentice Hall, Inc., 1979, pp. 364–369.

Wolfe, William L., "The Infrared Handbook,", Office of Naval Research, Department of the Navy, Washington, D.C., 1978, pp. 22–63 through 22–77.

Gonzalez, Rafael C., et al., "Digital Image Processing," Second Edition, Addison–Wesley Publishing Company, 1987, pp. 52–54.

Foley, J.D., et al., "Geometrical Transformations," *Fundamentals of Interactive Computer Graphics, The Systems Programming Series*, Addison–Wesley Publishing Company, 1982, pp. 245–266.

SCANNED IMAGE
COORDINATE SYSTEM

SURGICAL PROBE
COORDINATE SYSTEM

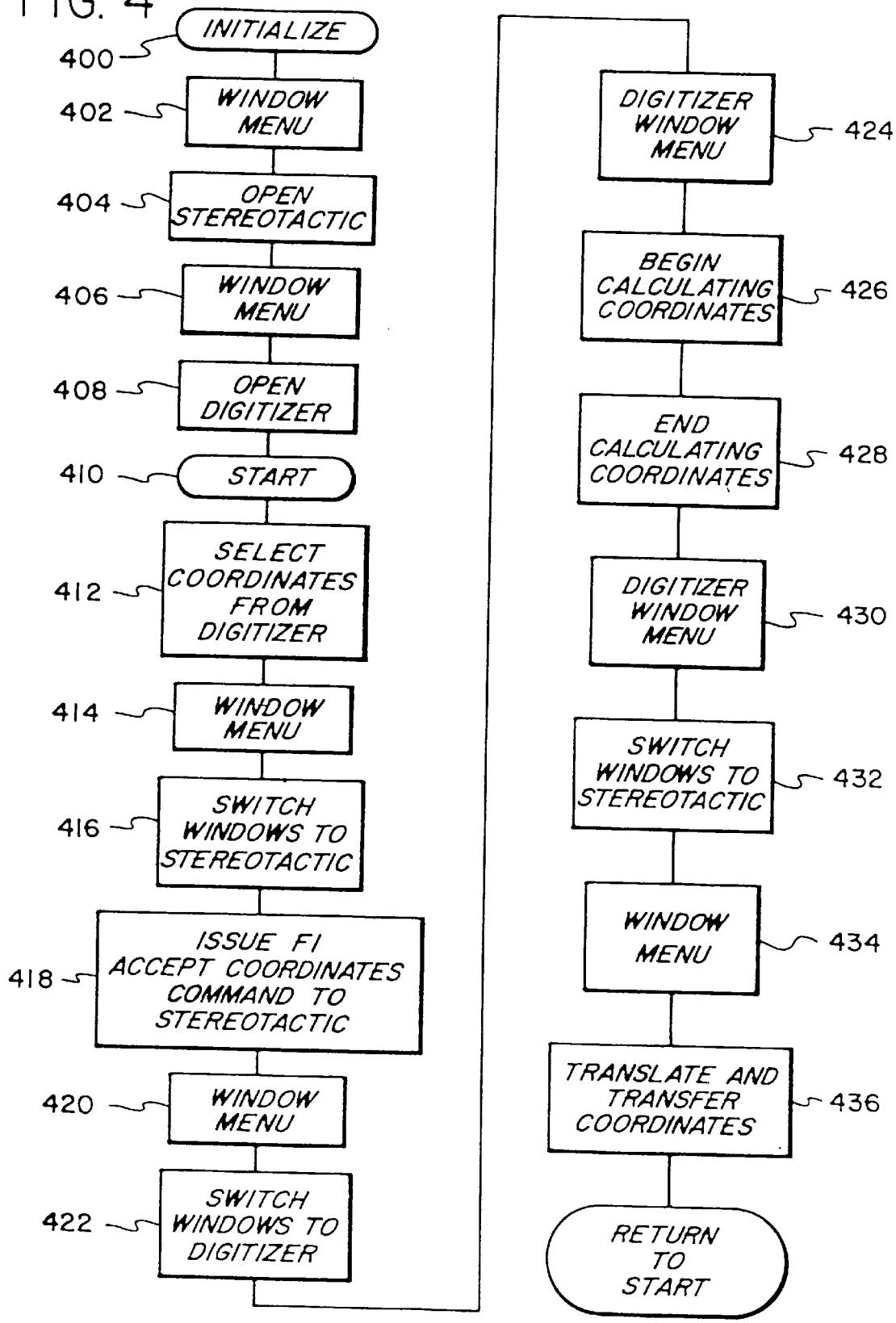

SYSTEM FOR INDICATING THE POSITION OF A SURGICAL PROBE WITHIN A HEAD ON AN IMAGE OF THE HEAD

This is a continuation of application Ser. No. 07/858,980 filed on May 15, 1992 now abandoned which is a continuation-in-part of application Ser. No. 07/600,753 filed on Oct. 19, 1990, now abandoned.

BACKGROUND OF THE INVENTION

Precise localization of position has always been critical to neurosurgery. Knowledge of the anatomy of the brain and specific functions relegated to local areas of the brain are critical in planning any neurosurgical procedure. Recent diagnostic advances such as computerized tomographic (CT) scans, magnetic resonance imaging (MRI) scanning, and positron emission tomographic (PET) scanning have greatly facilitated preoperative diagnosis and surgical planning. However, the precision and accuracy of the scanning technologies have not become fully available to the neurosurgeon in the operating room. Relating specific structures and locations within the brain during surgery to preoperative scanning technologies has previously been cumbersome, if not impossible.

Stereotactic surgery, first developed 100 years ago, consists of the use of a guiding device which channels the surgery through specific parts of the brain as localized by preoperative radiographic techniques. Stereotactic surgery was not widely used prior to the advent of modern scanning technologies as the injection of air into the brain was required to localize the ventricles, fluid containing chambers within the brain. Ventriculography carried a significant complication rate and accuracy in localization was marginal.

SUMMARY OF THE INVENTION

It is an object of this invention to provide a system which can determine the position of a probe within a head and display an image corresponding to the determined position.

The invention comprises a system for determining a position of a tip of a probe, which is positioned within an object, relative to cross sectional images of the object. The system comprises measuring means, translating means and selecting and displaying means. The measuring means measures the position of the tip of the probe relative to the object. The translating means translates the position of the tip of the probe relative to the object into a coordinate system corresponding to the cross sectional images of the object. The selecting and displaying means selects the image of the object which corresponds to the measured position of the tip of the probe relative to the object and displays the selected image.

The invention also comprises a system for determining a position of a tip of a surgical probe, which is positioned within a head of a body of a patient, relative to cross sectional images of the head. Means measures the position of the tip of the surgical probe relative to the head. Means translates the position of the tip of the surgical probe relative to the head into a coordinate system corresponding to the cross sectional images of the head. Means selects the image of the head which corresponds to the measured position of the tip of the surgical probe relative to the head and displays tile selected image.

The invention also comprises a method for determining a position of a tip of a surgical probe, which is positioned within a head of a body of a patient, relative to cross sectional images of the head, said method comprising the steps of: measuring the position of the tip of the surgical probe relative to the head; translating the position of the tip of the surgical probe relative to the head into a coordinate system corresponding to the cross sectional images of the head; selecting the image of the head which corresponds to the measured position of the tip of the surgical probe relative to the head; and displaying the selected image.

The invention also comprises a system for determining a position of an ultrasound probe relative to a head of a body of a patient when the probe is positioned adjacent to the head. An array is positioned adjacent the probe. First means determines the position of the ultrasound probe relative to the array. Second means determines the position of the head relative to the array. Means translates the position of the ultrasound probe into a coordinate system corresponding to the position of the head.

Other objects and features will be in part apparent and in part pointed out hereinafter.

BRIEF DESCRIPTION OF THE DRAWINGS

FIG. 4 is a flow chart of the translational software for translating coordinates from the surgical probe coordinate system to the scanned image coordinate system according to the invention.

Corresponding reference characters indicate corresponding parts throughout the several views of the drawings.

DETAILED DESCRIPTION OF THE PREFERRED EMBODIMENTS

With the advent of modern scanning equipment and techniques, several stereotactic systems have been developed and are presently available. These stereotactic systems allow a surgeon to localize specific points detected on CT, MRI or PET scans which have been previously generated prior to the surgical procedure being performed. In particular, the stereotactic systems allow the selection of specific points detected on the scans to be localized within the brain by the surgeon during the surgical procedure using a mechanical device.

Figure 1A:
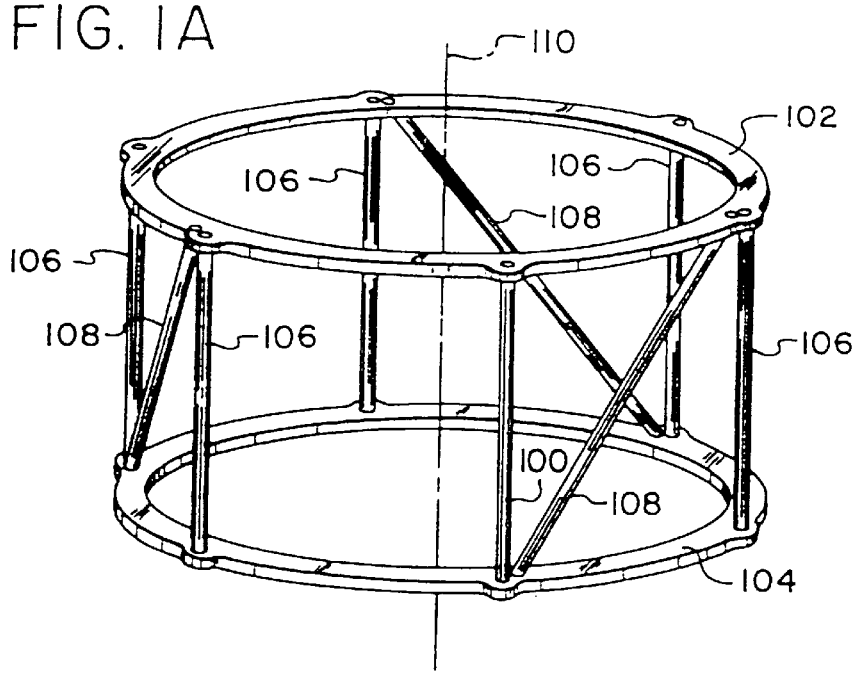
FIG. 1A is a perspective illustration of a cylindrical frame structure which is mounted around a patient's head during the scanning process.
Figure 1B:
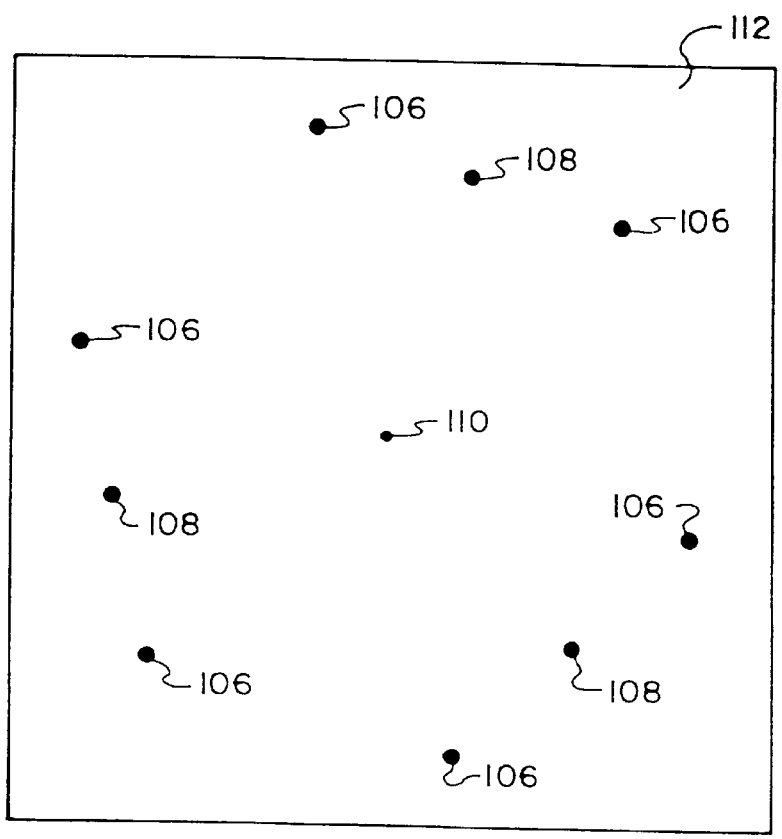
FIG. 1B is a plan view of the rods of the cylindrical frame structure of FIG. 1A taken along a plane midway between the upper and lower rings.

Initially, prior to the operative procedure, some form of localizing device, such as a frame, is attached to the patient's skull using sharp pins. The particular scan or scans which are to be performed are then generated with the head of the patient encircled by the frame. For example, the frame may be comprised of a cylindrical structure 100 as illustrated in perspective in FIG. 1A. Structure 100 includes an upper circular ring 102 and a lower circular ring 104 which are interconnected by six vertical rods 106 and three diagonal rods 108. The three diagonal rods 108 diagonally interconnect rings 102 and 104 so that any plane which passes through the cylindrical structure 100 and orthogonally intersects its axis 108 will intersect each of the diagonal rods 108 at a particular point. The resultant spacing between the diagonal and upright rods defines a unique plane within the cylindrical structure 100. For example, as shown in FIG. 1B, a scan in a particular plane would show a pattern of nine cross sectional views of the rods 106 and 108. The unique spacing of these views of the rods, as shown in plane 112 of FIG. 1B, would necessarily indicate that the position of the scan plane 112 was parallel to and midway between rings 102 and 104 of the cylindrical structure 100.

Figure 1C:
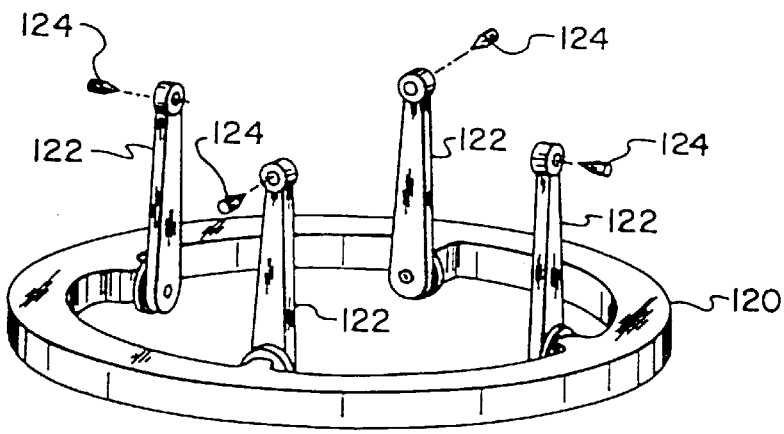
FIG. 1C is a perspective illustration of a reference ring which is mounted by uprights to a patient's head to support the cylindrical frame structure of FIG. 1A.

As a result of the scanning process, the images obtained are analyzed and the position within the images of the specific marking rods 106 and 108, called fudicels, are identified and measured. By measuring the distance between the rods 106, the specific location of a scan with reference to a base plane can be identified. Generally, the lower ring 104 of the cylindrical structure 100 is attached to a reference ring 120 (also known as a BRW head ring) as illustrated in FIG. 1C. As noted above, this ring 120 is supported on the patient's head via uprights 122 attached to the head by the use of sharp pins 124 so that the ring 120 is held firmly in place with respect to the head. The lower ring 104 of the cylindrical structure 100 is mounted to the reference ring 120 attached to the patient's head so that these two rings are in parallel planes.

Figure 1D:
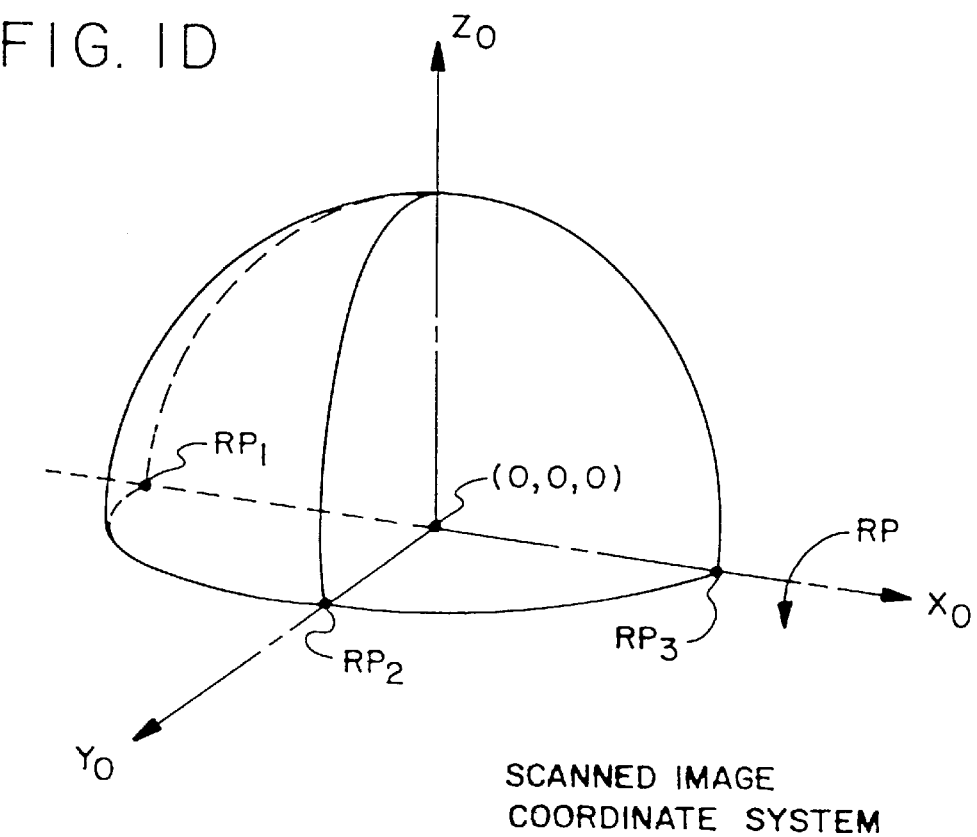
FIG. 1D is a perspective illustration of the coordinate system of a three dimensional scanned image.

As shown in FIG. 1D, the scanning system (e.g., CT, MRI, PET) which is performing the scanning has a scanned image coordinate system ($X_0$, $Y_0$, $Z_0$) within which a reference plane RP can be defined by at least three reference points RP1, RP2 and RP3 located on the head 124 of the patient. A computer is then used to calculate a specific position within the brain and a target picked out on the specific image can be approached with a fair degree of accuracy during the surgical procedure.

Although stereotactic surgery allows a surgeon to be guided to a specific point with accuracy, it has not been particularly useful in allowing the surgeon to identify the particular location of a surgical probe within the brain at any point during the surgical process. Frequently in neurosurgery, brain tumors or other target points within the brain are indistinguishable from surrounding normal tissue and may not be detected even with the use of frozen sections. Moreover, with modern microsurgical techniques, it is essential that the neurosurgeon identify specific structures within the brain which are of critical functional importance to the patient. In addition, the boundaries of these structures must be accurately defined and specifically known to the surgeon during the surgical process. In this way, these tissues will not be disturbed or otherwise damaged during the surgical process resulting in injury to the patient.

Figure 2A:
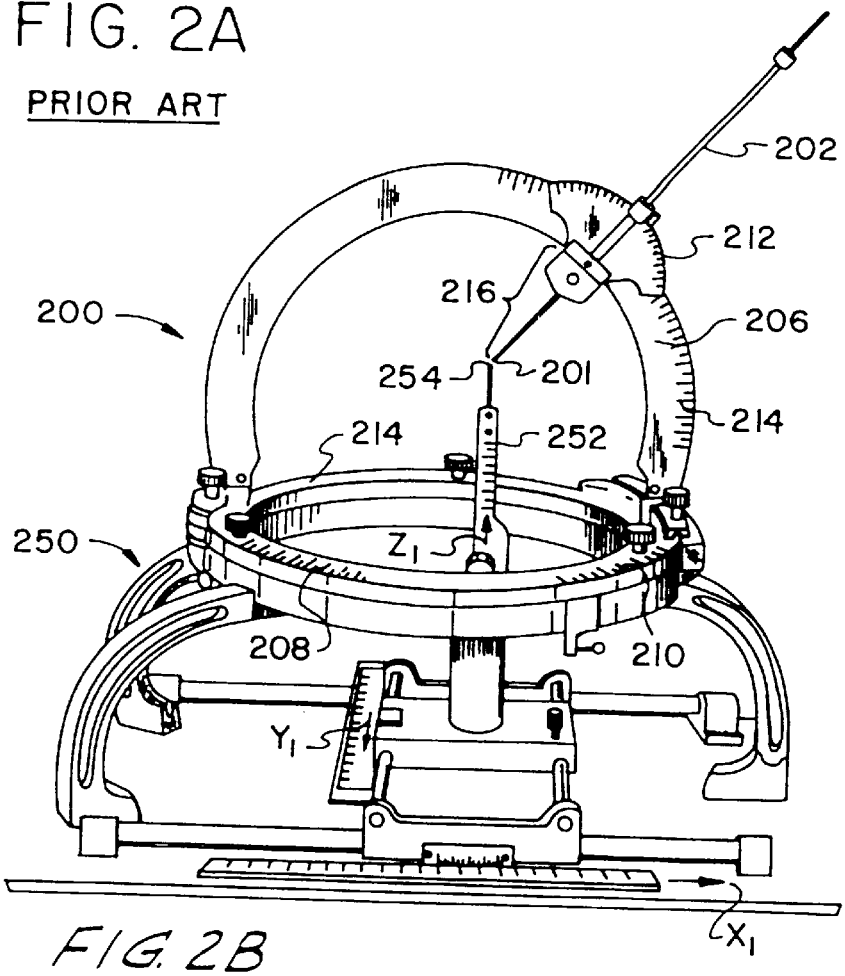
FIG. 2A is a perspective view of the caliper frame used in the prior art to determine the relative position between a position in the head and the phantom base.
Figure 2B:
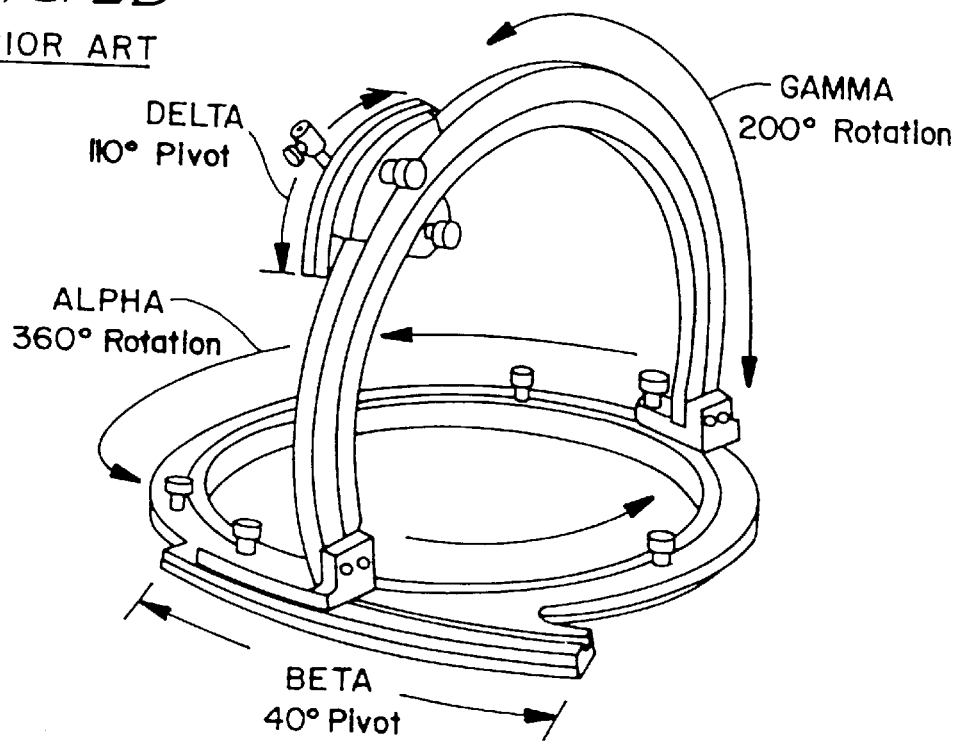
FIG. 2B is a perspective view of the prior art caliper frame of FIG. 2A illustrating its angles of adjustment.

In the past, the surgeon has been able to use the stereotactic system in reverse in order to permit the determination of the position of a surgical probe relative to the scanned images so the image corresponding to the probe position can be identified and viewed. However, going in reverse from the patient's brain backwards to find the position of the surgical probe relative to the scan is a cumbersome and time-consuming process. Usually, a specially designed caliper frame 200, as illustrated in FIG. 2A, has to be attached to the ring 120 affixed to the patient's head to determine the position of the surgical probe in the head. For example, suppose the surgeon desires to know the position of a tip 201 of a probe 202 in the patient's head. First, the caliper frame 200 is fitted to the reference ring 120 affixed to the patient's head. Next, the position of probe 202 is positioned on arch 206 and the frame 200 is set to indicate the alpha, beta, gamma and delta angles on scales 208, 210, 212 and 214 that the probe 202 defines with respect to the frame 200, as shown in FIG. 2B. Next, the distance 216 from the tip of the probe 202 to the arch 206 is determined.

The caliper frame 200 is then transferred and mounted to a phantom base 250 in a manner as illustrated in FIG. 2A. The phantom base 216 has a coordinate system ($X_1$, $Y_1$, $Z_1$). Generally, the caliper frame 200 identifies a point 201 over the phantom base 250. A pointing device 252 is positioned to have its tip 254 at point 201. The $X_1$-$Y_1$ plane of the phantom base 200 corresponds to a plane parallel to the plane in which the reference points RP1, RP2 and RP3 are located. The ($X_1$, $Y_1$, $Z_1$) coordinates define the position of point 201. As a result, the position of point 254 with respect to the $X_1$-$Y_1$ plane and, therefore, with respect to the reference plane RP is now known. A computer can now be used to calculate the specific position within the brain and the particular scan which corresponds to the calculated position can now be accessed and viewed on a scanning system.

Figure 2C:
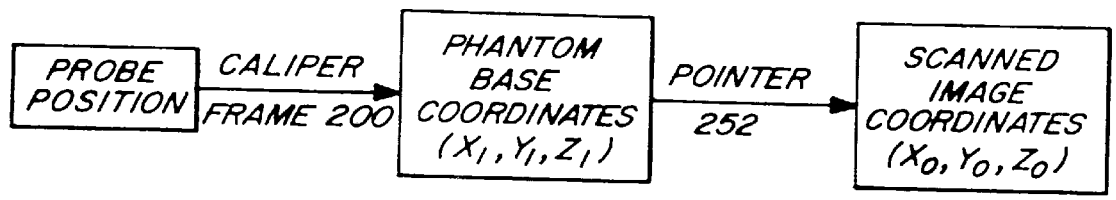
FIG. 2C is a block diagram of the steps involved in the prior art process of determining the position of surgical probe relative to the scanned images so that the image corresponding to the probe position can be identified and viewed by the surgeon.

In summary, this prior art process as shown in FIG. 2C identifies the location of the tip 201 of the surgical probe 202 for the surgeon. Initally, the surgeon positions the probe 202 on the caliper frame 200, which is attached to the head, at the position desired within the head. The caliper frame 200 is then removed from the patient's head and transferred to the phantom base 250. The pointing device 252 is then positioned at point 254 which is essentially coaxial with point 201 of the tip of the probe. The pointing device 252 then indicates the position of the tip of the probe in the phantom base coordinate system ($X_1$, $Y_1$, $Z_1$). Finally, these coordinates are used to determine the scanned image coordinates ($X_0$, $Y_0$ $Z_0$) so that the image corresponding to the probe position can be displayed.

After this cumbersome and time-consuming process, the surgeon has now determined the position of the tip 201 of the probe 202 with respect to the scanned images and can now view the image corresponding to the probe position to decide the next step in the surgical procedure. This entire process takes approximately ten to fifteen minutes and increases the risks of intraoperative contamination as the base of the calipers are nonsterile. Because of these considerations, stereotactic surgery is not commmonly employed in most procedures. Furthermore, the minimal accuracy it affords is generally insufficient for modern microsurgical techniques. Consequently, stereotactic surgery is not generally available to the majority of certain patients undergoing surgery.

Figure 2D:
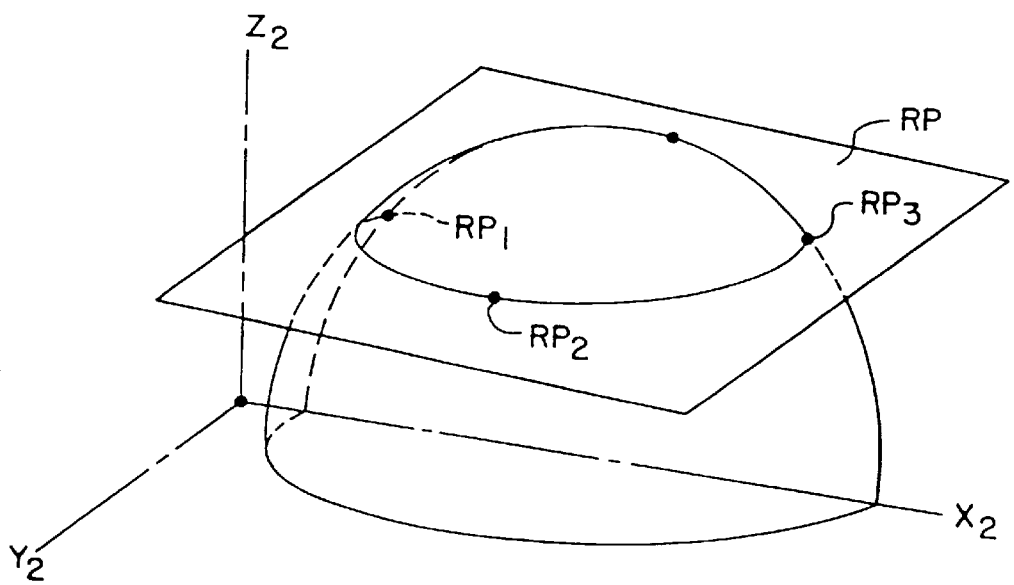
FIG. 2D is a perspective illustration of a three dimensional coordinate system of a surgical probe.

Comparing FIGS. 1D and 2A, it can be seen that it is necessary for the surgeon to know the specific location of the tip 201 of the surgical probe 202 with respect to the scanned image coordinate system $(X_0, Y_0, Z_0)$ of the particular scans that were preoperatively performed. In other words, the surgical probe 202 has a particular coordinate system $(X_2, Y_2, Z_2)$ which is illustrated in FIG. 2D. Ideally, the surgical probe coordinate system $(X_2, Y_2, Z_2)$ must be related to the scanned image coordinate system $(X_0, Y_0, Z_0)$. The prior art as illustrated in FIG. 2B has suggested relating these coordinate systems via the phantom base coordinate system $(X_1, Y_1, Z_1)$. However, as noted above, this relational process is inaccurate, time-consuming and cumbersome. The invention uses a 3D digitizer-system to locate the position of the tip 201 of the surgical probe 202 and to directly relate the surgical probe coordinate system $(X_2, Y_2, Z_2)$ to the scanned image coordinate system $(X_0, Y_0, Z_0)$.

Figure 3A:
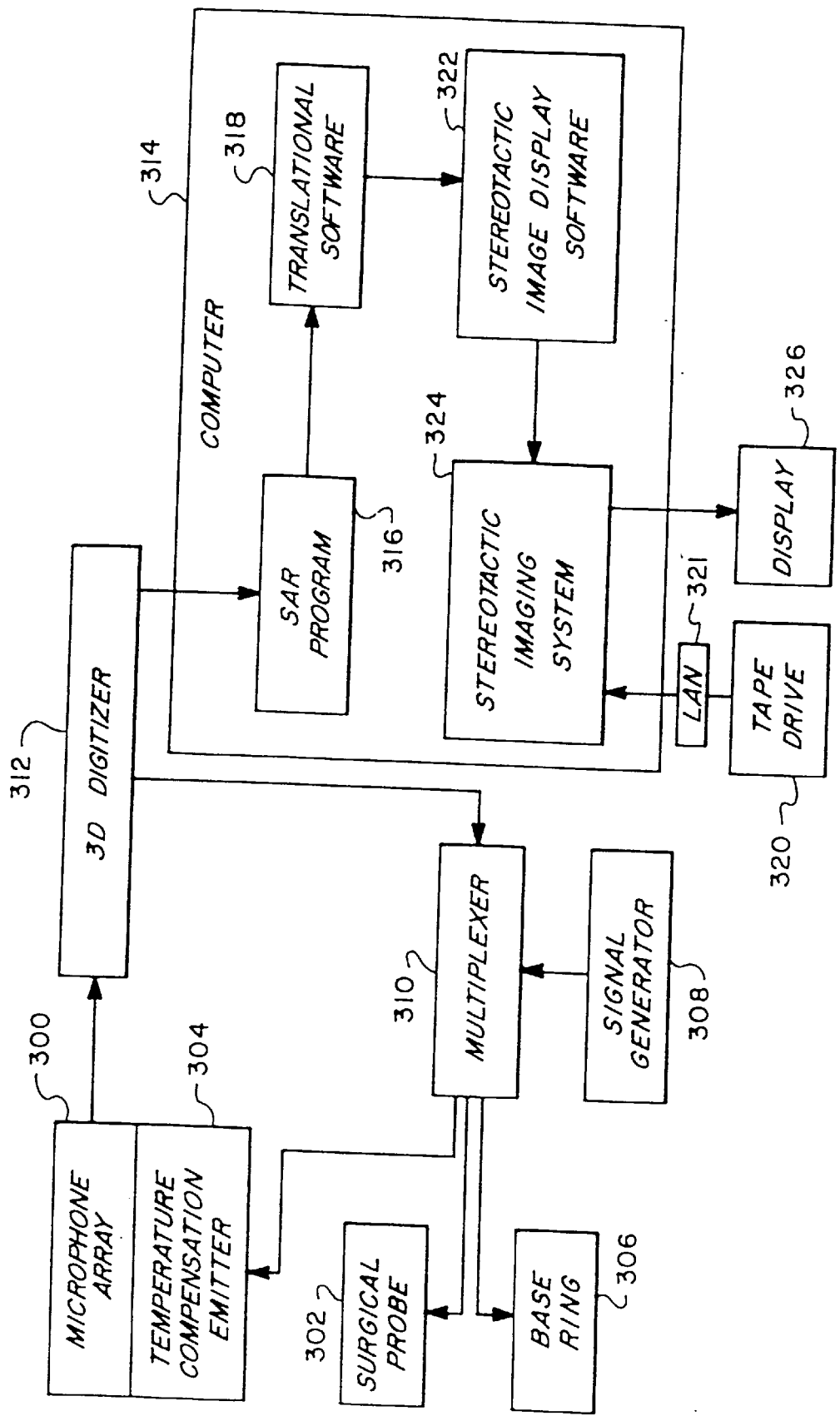
FIG. 3A is a block diagram of a system according to the invention for indicating the position of a surgical probe within a head on an image of the head.
Figure 3B:
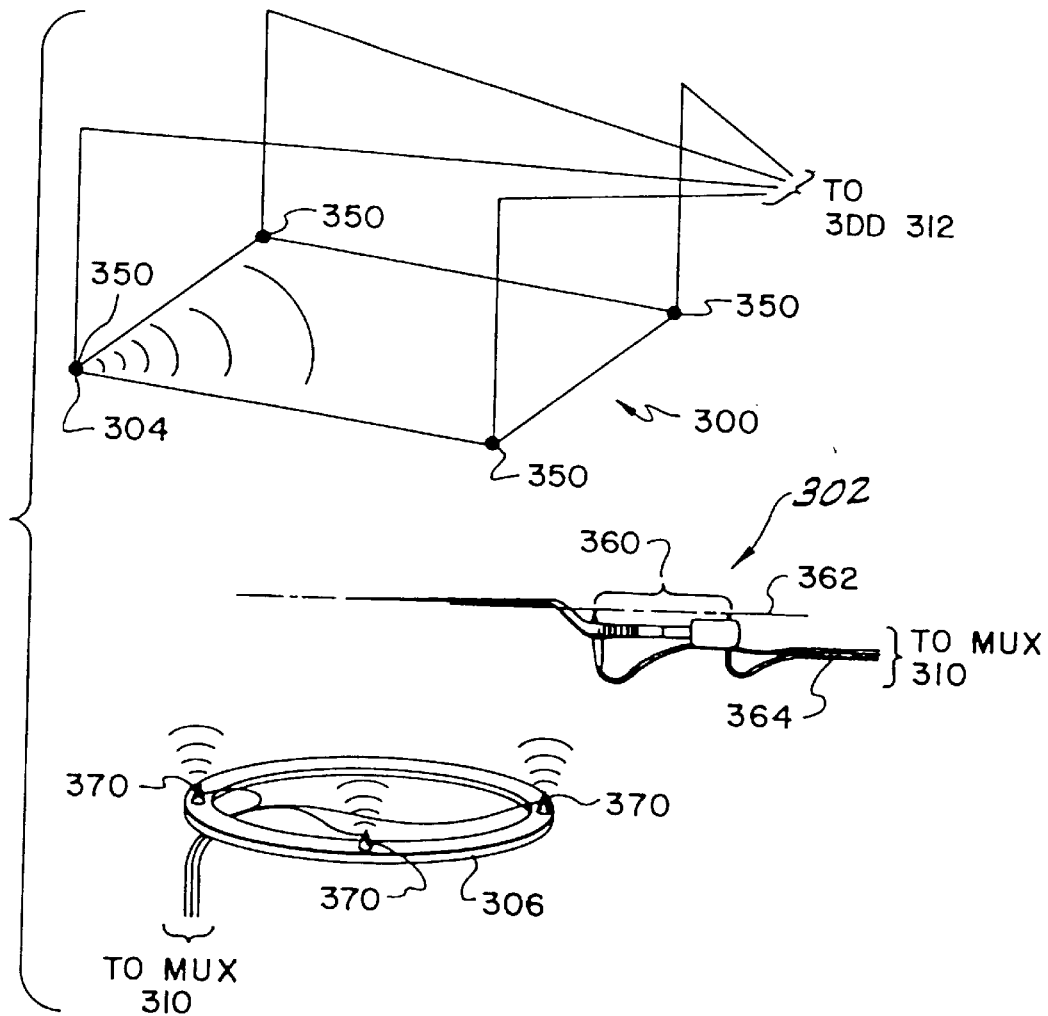
FIG. 3B is a perspective schematic diagram of the microphone array, surgical probe and base ring according to the invention.

In particular, an off-the-shelf, three dimensional sonic digitizer such as Model GP-8-3D produced by Scientific Accessories Corporation is used to determine the position of the probe. As shown in FIG. 3A, the 3D digitizer system includes a microphone array 300 which is generally mounted in the operating room on the ceiling or in some other position so that it is in a line of sight with the surgical probe 302 that is being used. As will be described in greater detail below, the probe 302 includes transmitters such as sound emitters thereon which interact with the microphone array 300 so that the position of the tip of surgical probe 302 is known at any particular instant in time. The 3D digitizer system also includes a temperature compensation emitter 304 associated with the microphone array 300. Furthermore, mounted to the ring 120 (FIG. 1C) affixed to the patient's head is a base ring 306 which is coaxial and parallel with the plane defined by reference ring 120. This base ring 306 includes a plurality of transmitters as will be described below which interact with the microphone array 300 so that the relative position of the base ring 306 can be determined any particular instant in time. Signal generator 308 generates a signal which is provided through a multiplexer 310 to the temperature compensation emitter 304, surgical probe 302, and base ring 306. Usually, temperature compensation emitter 304 is activated by the signal generator 308 via multiplexer 310 to emit a signal which is received by the microphone array 300. Each of the signals received by each of the microphones of the array 300 is provided to a digitizer 312 which digitizes the signals and provides the digitized signals to computer 314 which includes a spatial acquisition and recording (SAR) program 316 which acquires and records spatial coordinates based on the digitized signals. For example, program 316 may be the SACDAC program licensed by PIXSYS of Boulder, Colorado. This program evaluates the digitized signals emitted by the temperature compensation emitter 304 to determine the reference standards. i.e., the velocity of the radiation through the air. For example, depending on the temperature of the air in the operating room, the period of time that it takes from the instant that the temperature compensation emitter 304 is actuated to radiate a signal until the instant that each of the microphones of the array 300 receives the emitted signal will vary. The SAR program 316 knows, through calibration, the distance between the temperature compensation emitter 304 and each of the microphones of the array 300. Therefore, the SAR program 316 can immediately calculate the velocity of the signals being transmitted. This velocity establishes a reference for determining the position of the surgical probe 302 and the base ring 306.

Next, the emitters of the base ring 306 are activated so that the position of the base ring 306 can be determined. At this point, the emitters of the base ring 306 are successively energized and the radiation transmitted by these emitters is detected by the microphone array 300. The signal generated by the microphones from this radiation is digitized and evaluated by the SAR program 316 to determine the position of each of the emitters of the base ring 306. Once the positions of the base ring emitters have been determined by the SAR program 316, standard geometrical computations are performed by the SAR program to determine the plane defined by the base ring 306 with respect to the microphone array 300.

Digitizer 312 then signals multiplexer 310 to provide the signal generated by signal generator 308 to the surgical probe 302. At this point, the emitters of the surgical probe 302 are successively energized and the radiation transmitted by these emitters is detected by the microphone array 300. The signal generated by the microphones from this radiation is digitized and evaluated by the SAR program 316 to determine the position of each of the emitters of the surgical probe 302. Once the positions of the probe emitters have been determined by the SAR program 316, standard geometrical triangulation is performed by the SAR program to determine the location of the tip of the surgical probe with respect to the microphone array 300.

Therefore, by using the 3D digitizer system, the position of the base ring 306 and the position of the surgical probe 302 relative to the base ring 306 can be determined by the SAR program 316. As noted above, the base ring 306 is mounted to the reference ring 120 (FIG. 1C) and is essentially coplanar therewith so that the base ring 306 defines the reference plane RP of the scanned image coordinate system illustrated in FIG. 1D.

Computer 314 includes translational software 318 which then translates the coordinates of surgical probe coordinate system illustrated in FIG. 2D into the scanned image coordinate system illustrated in FIG. 1D. As a result of this translation, computer 314 has now determined the particular scanned image of the preoperative scan on which the tip of the surgical probe 302 would be located. The system includes a tape drive 320, accessed through a local area network (LAN) 321, in which each of the images of the preoperative scan are stored. The translated coordinates generated by translational software 318 are provided to the stereotactic image display software 322, also resident within computer 314, and identify the particular scanned image which is to be viewed by the surgeon. The identified image is selected by the stereotactic imaging system 324 which recreates the image from the data stored in tape drive 320 and displays it on a high resolution display 326. Steteotactic image display software 322 and stereotactic image system 324 may be any off-the-shelf system such as manufactured by Stereotactic Image Systems, Inc. of Salt Lake City, Utah.

Referring to 3B, a perspective illustration of the microphone array 300, temperature compensation emitter 304, surgical probe 302 and base ring 306 are illustrated. Microphone array 300 includes a plurality of microphones 350, the outputs of which are connected to 3D digitizer 312. Adjacent to the microphone array 300 is a temperature compensating emitter 304 which selectively emits signals used by the SAR program in calibration to determine the velocity of the radiation. For example, in the Scientific Accessories Corporation Model GP-8-3D, a sonic digitizer is used. In this case, the speed of sound being transmitted from the temperature compensation emitter 304 to the microphones 350 is calculated by the SAR program to determine the speed at which the sound is being transmitted through the air. Since this system is very accurate and the speed of sound varies fairly significantly with respect to the temperature of the air, the temperature compensation emitter 304 allows the 3D digitizer system to compensate for changes in the air temperature in the operating room. Surgical probe 302 comprises a bayonet surgical forceps modified to carry at least two sound emitters 360 thereon which are essentially coaxial on axis 362 with the tip of the forceps. The emitters are in line and immediately below the surgeon's line of sight through the forceps so that the line of sight is not blocked. In general, the microphone array 350 is attached to the operating light above the patient's head so that it is in direct line of sight with the forceps as they are being used by the surgeon. The microphones 350 listen to the sound emitted from the sequential energization of the emitters 360 on the forceps. The SAR software 316 measures the time of transmission from each of the sound emitters 360 on the forceps to the microphones 350. By comparing these times, the position of both emitters 360 and, therefore, the tip of the forceps can be calculated by the SAR program 316.

Base ring 306 is affixed to the reference ring 120 attached to the patient's head and is essentially coplanar with the reference points RP1, RP2 and RP3. Base ring 306 includes a plurality of emitters 370 thereon which are connected to multiplexer 310 and energized by signal generator 308. Each one of these emitters 370 is sequentially energized so that the radiation emitter thereby is received by the microphones 350 of array 300. The emitters 370 are preferably positioned 90° apart with the center emitter being located at the anterior of the head. This permits base ring 306 to be mounted around the head so that all three emitters are in line of sight with the array. The resulting signals are digitized by digitizer 312 so that the SAR program 316 is able to determine the plane in which the emitters 370 are located. This plane essentially defines the reference plane because it is coplanar with the reference points RP1, RP2 and RP3. By determining the position of the reference plane, translational software 318 is now able to take the coordinate position of the probe 302 and translate it from the surgical probe coordinate system of FIG. 2D into the scanned image coordinate system as illustrated in FIG. 1D As a result, the particular scanned image which corresponds to the position of the probe can be identified and displayed for viewing by the surgeon.

The surgical probe 302 is generally a bayonet cauterizing device which has a bundle of wire 364 attached thereto. Therefore, the wires required to connect the emitters 360 to the multiplexer 310 are part of the bundle of wires 364 which connect the forceps to its electrical power source and the surgeon is familiar with handling such forceps connected to a wire bundle. Therefore, there is no inconvenience to the surgeon in using such a probe and the surgeon is familiar with handling such a forceps connected to a wire bundle.

Base ring 306 is one apparatus for determining and positioning the reference points RP1, RP2 and RP3 with respect to the microphone array 300. An advantage of the base ring 306 is that each time the patient's head is moved the base ring 306 is energized to define the reference plane. This allows the surgeon to move the patient's head during surgery. Alternatively, the reference points RP1, RP2 and RP3 can be established by using a reference mode of the 3D digitizer 312. In particular, the tip of probe 302 is positioned on each of the reference points RP1, RP2 and RP3 and actuated to emit a signal to the microphone array 300 so that the position of the tip can be determined at each of these points. This is performed during a reference mode of operation of the 3D digitizer 312 so that the SAR program 316 calculates, at the end of the execution of this mode, the position of the reference points RP1, RP2 and RP3. This requires that the reference points have to be reestablished before the position of the surgical probe is determined to avoid changes in the reference plane due to movement of the head. On the other hand, one advantage of this approach is that the use of the reference ring 120 may be eliminated. In particular, it is possible that the reference pins 122 can be permanently affixed to the skull of the patient. For example, these pins may be radiolucent surgical screws which are embedded in the patient's skull and which have radiopaque tips. These screws would be affixed to the patient's skull before surgery and before the preoperative scanning so the radiopaque tips would provide a constant reference during scanning and throughout the stereotactic surgical procedure. During the actual surgery, the probe would be used to indicate the position of each of the radiopaque tips before the probe position was determined. By eliminating the need for the reference ring 120, other advantages are also achieved. For example, generally the preoperative scanning must be done under anesthetic because the reference ring 120 interferes with intubation. Therefore, intubation must occur before the reference ring is affixed to the skull. By eliminating the need for the reference ring 120 and using surgical screws to identify the reference points RP1, RP2 and RP3, the preoperative scanning can be performed without the need for intubation and the anesthesia accompanying it. In one alternative embodiment, it is contemplated that the emitters 370 may each be separately mounted to a screw or other fixed structure positioned at one of the reference points.

Figure 3C:
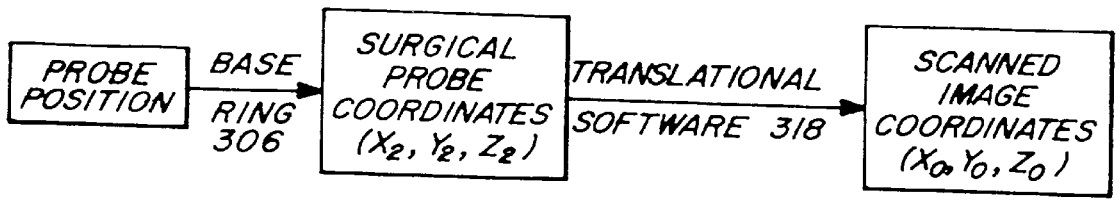
FIG. 3C is a block diagram of the steps involved in the process according to the invention for determining the position of a surgical probe relative to the scanned images so that the image corresponding to the probe position can be identified and viewed by the surgeon.

In summary, this process according to the invention is illustrated in FIG. 3C and identifies the location of the tip of the surgical probe 202 for the surgeon. Initially, the reference plane is determined by energizing the base ring 306 or by positioning the probe 302 at the reference points (as described herein). Next, the surgeon positions the probe in the position desired within the head. The emitters of the probe are then energized so that the probe position is measured and determined in the surgical probe coordinate system $(X_2, Y_2, Z_2)$. Next, the translational software 318 converts the surgical probe coordinate system into the scanned image coordinate system $(X_0, Y_0, Z_0)$ so that the image corresponding to the probe position can be displayed.

Figure 3D:
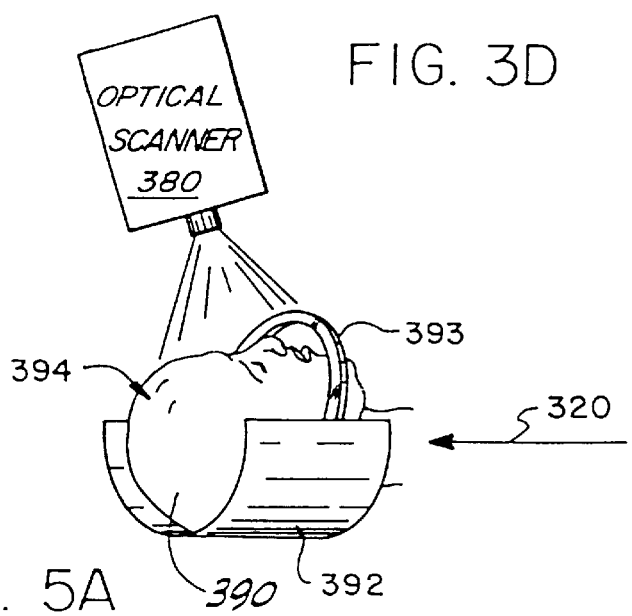
FIG. 3D is a perspective schematic diagram of an optical scanner used in combination with a cradle.

Referring to FIG. 3D), a perspective illustration of a patient's head 390 in a cradle 392 during the scanning process is shown. As will be described below, optical scanner 380, having emitters 381 thereon, is employed to determine the position of the head 390 relative to a cradle 392 positioned on the head.

Referring to 3E, a perspective illustration of the microphone array 300, temperature compensation emitter 304, surgical probe 302 and optical scanner 380 are illustrated. Microphone array 300 includes a plurality of microphones 350, the outputs of which are connected to 3D digitizer 312. The microphone array 300 provides a fixed frame of reference to which the position of probe 302 is measured and to which the position of the head 390, relative to the cradle 392, is measured. As a result, the position of the probe 302 relative to the head 390 at any instant in time can be determined.

Adjacent to the microphone array 300 is a temperature compensating emitter 304 which selectively emits signals used by the SAR program in calibration to determine the velocity of the radiation. For example, in the Scientific Accessories Corporation Model GP-8-3D, a sonic digitizer is used. In this case, the speed of sound being transmitted from the temperature compensation emitter 304 to the microphones 350 is calculated by the SAR program to determine the speed at which the sound is being transmitted through the air. Since this system is very accurate and the speed of sound varies fairly significantly with respect to the temperature of the air, the temperature compensation emitter 304 allows the 3D digitizer system to compensate for changes in the air temperature in the operating room.

Surgical probe 302 comprises a bayonet surgical forceps modified to carry at least two sound emitters 360 thereon which are essentially coaxial on axis 362 with the tip of the forceps. The emitters are in line and immediately below the surgeon's line of sight through the forceps so that the line of sight is not blocked. In general, the microphone array 350 is attached to the operating room light above the patient's head so that it is in direct line of sight with the forceps as they are being used by the surgeon. The microphones 350 listen to the sound emitted from the sequential energization of the emitters 360 on the forceps. The SAR software 316 measures the time of transmission from each of the sound emitters 360 on the forceps to the microphones 350. By comparing these times, the position of both emitters 360 and, therefore, the tip of the forceps can be calculated by the SAR program 316.

Optical scanner 380 is generally located over the patient's head 390 and is used during scanning to establish the position of the head 390 relative to the cradle 392 thereby to relate the frame of reference of the cross sectional scans to the forehead 394. Scanner 380 is also used during surgery to establish the position of the head 390 relative to the cradle 392 thereby to relate the frame of reference of the probe 302 to the forehead 394.

During the preoperative scanning process as shown in FIG. 3D, when the cross sectional images of the head are created, the patient's head lies temporarily in cradle 392. The cradle includes an arc 393 of radiopaque material so that it appears in at least some of the cross sectional scans. As a result, the arc 393 defines a plane relative to the head 390. During scanning, this plane can be defined as the 0,0,0 plane for convenience. After the head is placed in the cradle, optical scanner 380 is used to establish the position of the cradle 392 and its attached arc 393 relative to the forehead 394. In particular, the optical scanner 380 scans both the forehead and the arc 393 of the cradle 392 and, via computer 396 employing forehead fitting software 398, determines the position of the arc 393 of the cradle 392 relative to the forehead 394. The forehead fitting software may be any off-the-shelf or custom software which graphs a set of points so that a curve defining the contour of the forehead can be calculated, a curve defining the arc can be calculated, and a curve defining the relative position of the forehead and the arc can be calculated. Since the position of the cross sectional scans relative to the radiopaque arc 393 is known (because the cradle arc defines the 0,0,0 plane) and since the position of the arc 393 of the cradle 392 relative to the forehead 394 is known (because of the scanning by the optical scanner), then the position of the cross sectional scans relative to the forehead is known and can be calculated by translational software 316.

During surgery, a base ring 306 is firmly affixed to the head. The base ring 306 does not have to be positioned in the same location relative to the head as the arc was during the scanning process when the cross sectional images were created. The base ring 306 used during surgery includes emitters 370 which communicate with the array 300 to establish the position of the base ring 306. As a result, the base ring 306 defines a plane relative to the head 390. After affixing the base ring to the head, optical scanner 380 is used prior to or during the surgery to establish the position of the base ring 306 relative to the forehead 394. In particular, the optical scanner 380 scans both the forehead and the base ring 306 and, via computer 396 employing forehead fitting software 398, determines the position of the base ring 306 relative to the forehead 392. Since the position of the probe relative to the base ring is known (because of communication via the array) and since the position of the base ring relative to the forehead is known (because of the scanning by the optical scanner), then the position of the probe relative to the forehead is known and can be calculated by translational software 316. Since the position of the cross sectional images relative to the forehead is also known (from the preoperative scanning process), the end result is that the position of the probe relative to the cross sectional images is known so that the position of the tip of the probe on the closest cross sectional image can be displayed.

Optical scanner 380 and computer 396 are a standard, off the shelf scanner used to scan an object to determine its three-dimensional shape. For example, a limb scanner such as PIXSYS Optical Scanner used to develop three-dimensional models for artificial limbs may be used. The scanner 380 emits a laser beam or other optical beam toward the arc 393 and the forehead 394 and receives the light reflected there through an array of linear chip cameras such as CCD (charge coupled device) cameras. By evaluating the position of the reflected light using the camera array, the optical scanner 380, including a computer 396, determines the shape and, thus, the contour of the forehead 394, the shape of the arc 393 of cradle 392 and the relative position of the forehead and the arc 393. Computer 396 indicates to the translational software 316 of computer 314, which is a part of the system as illustrated in FIG. 3A, the position of the probe 302 relative to the forehead 392. The translational software 318 then coverts this indicated position into the coordinate system of the cross sectional scanned images. As a result, the particular scanned image which corresponds to the position of the probe can be identified and displayed on display 326 (FIG. 3A) for viewing by the surgeon.

The surgical probe 302 is generally a bayonet cauterizing device which has a bundle of wire 364 attached thereto. Therefore, the wires required to connect the emitters 360 to the multiplexer 310 are part of the bundle of wires 364 which connect the forceps to its electrical power source. Surgeons are generally familiar with handling such forceps connected to a wire bundle. Therefore, there is no inconvenience to the surgeon in using such a probe and the surgeon is experienced with handling such a forceps connected to a wire bundle.

One advantage of the optical scanner 380 is that it eliminates the need for a ring or pins to be attached to the patient's head during the preoperative scanning process. Each time the patient's head is placed in a cradle, the optical scanner 380 can be used to scan the head and cradle to redefine their relative position without the need for any contact. The reference ring (i.e., arc) on the head is, therefore, temporary. By eliminating the need for a permanent reference ring 120 or reference pins RP1–RP3, other advantages are also achieved. For example, generally the preoperative scanning must be done under anesthetic because the reference ring 120 interferes with intubation or it must be done after pins are affixed to the head. Therefore, intubation must occur before the reference ring is affixed to the skull. By eliminating the need for the permanent reference ring 120 and/or reference pins, and by using the contour of the forehead to define a reference point, the preoperative scanning can be performed without the need for intubation and the anesthesia accompanying it.

In summary, during the preoperative scanning process the patient simply lies in a U-shaped cradle attached to the end of a CT or MRI table. Above the patient's face is an arc providing the reference plane. All scans are obtained with reference to and preferably parallel to this arc defining the reference or base plane. The optical scanner relates the forehead contour to this arc so that the relation of the forehead to the scans is known.

In the operating room, the patient's head is again scanned with the optical scanner but this time the arc over the patient's head is base ring 306. The reference emitters attached to the base ring define the operative reference system. Therefore, the forehead is again related to the base ring by the optical scanner to define a new reference system; this time the new reference system is the operating room. The computer then matches the forehead contours obtained in the operating room and the scanning room to relate the two reference systems. In effect, the forehead is a "bridge" between the reference system of the preoperative scanner and the reference system of the operating room.

The cradle does not have to appear in the actual scans. The primary purpose of the cradle is to keep the patient's head from moving so that all scans are obtained with the same relationship to the arc.

Referring to FIG. 4, a flow chart of the operation of the translational software 318 is illustrated. Initially, the surgeon locates the probe 302 in the position which is to be determined. (If a base ring 306 is not being used to identify the location of the reference plane, the initial step is for the surgeon to use the reference mode of the 3D digitizer 312 to identify the reference plane by locating the surgical probe tip at several points in the plane.)

The system initializes at step 400 so that translational software opens a window menu at step 402 of a multitasking program such as DESQ VIEW distributed by Quarterdeck Office Systems of Santa Monica, Calif. Such software permits simultaneous execution of multiple software programs. In general, once a program is selected for actuation, it continues to run either in the foreground or in the background until deactuated.

The translational software continues initializing by selecting the stereotactic imaging system and actuating the stereotactic imaging system in the foreground by opening the stereotactic window at step 404. Thereafter, the translational software returns to the window menu at step 406 moving the stereotactic image display software to the background and selects the digitizer window at step 408 to actuate the digitizer in the foreground. The computer is then ready to be actuated by the foot switch.

The surgeon then actuates a foot pedal or other switch which indicates that the system should perform a computation. Actuation of the foot switch is essentially the beginning of the start step 410. Upon actuation, the digitizer energizes calibration by the temperature compensation emitter 304 to determine the velocity of the sound waves, energizes the emitters of the base ring 306 to locate the reference plane and energizes the emitters of the surgical probe 302 to locate the position of the tip of the probe 302. The signals generated by the microphone array are digitized so that the SAR program 316 determines the coordinates of the tip of the surgical probe. At step 412, the translational software 318 selects the coordinates from the SAR program.

Next, the window menu is again accessed at step 414 and the window menu switches to the stereotactic image system software to the foreground at step 416 to specifically control the operation of the stereotactic imaging system 324. At this point, the translational software 318 issues an F1 command to the stereotactic image display software 322 which in turn prepares the stereotactic imaging system 324 to accept coordinates. At step 420, the window menu is again selected so that at step 422 the computer switches the digitizer window into the foreground. At step 424, the digitizer window menu is accessed and coordinate translation is selected. At step 426, the digitizer begins calculating the coordinates and at step 428 the coordinate calculation is ended. The translational software then returns to the digitizer window menu at step 430, switches windows to place the stereotactic image system software in the foreground at 432 to prepare it for receiving the coordinates and again returns to the main window menu at step 434. Finally, the coordinate information is translated, including any necessary manipulation, and transferred to the stereotactic image display software 322 at step 436 which actuates the stereotactic imaging system 324 to select the particular image from the tape drive 320 and display it on high resolution display 326. The stereotactic image display software 322 instructs the stereotactic imaging system 324 to display the image closest to transferred coordinates and to display a cursor on the display 326 at the coordinates which corresponds to the position of the tip of the probe. Thereafter, the computer 314 is in a standby mode until the foot switch of the surgeon is again actuated to execute the translational software beginning with the start step 410.

The translation that occurs in step 436 depends on the position of the surgical probe coordinate system relative to the scanned image coordinate system and the units of measure. In the preferred embodiment, the systems are coaxial and the units of measure are the same so that algebraic adjustment is unnecessary. However, it is contemplated that the coordinates systems may not be coaxial, in which case translation would require arithmetic and/or trigonometric calculations. Also, the sequence, e.g., $(X_2, Y_2, Z_2)$, in which the coordinates are generated by the digitizer may be different than the sequence, e.g., $(X_0, Y_0, Z_0)$, in which stereotactic image system software receives coordinates. Therefore, the sequence in which the coordinates are transferred may have to be reordered.

Figure 5A:
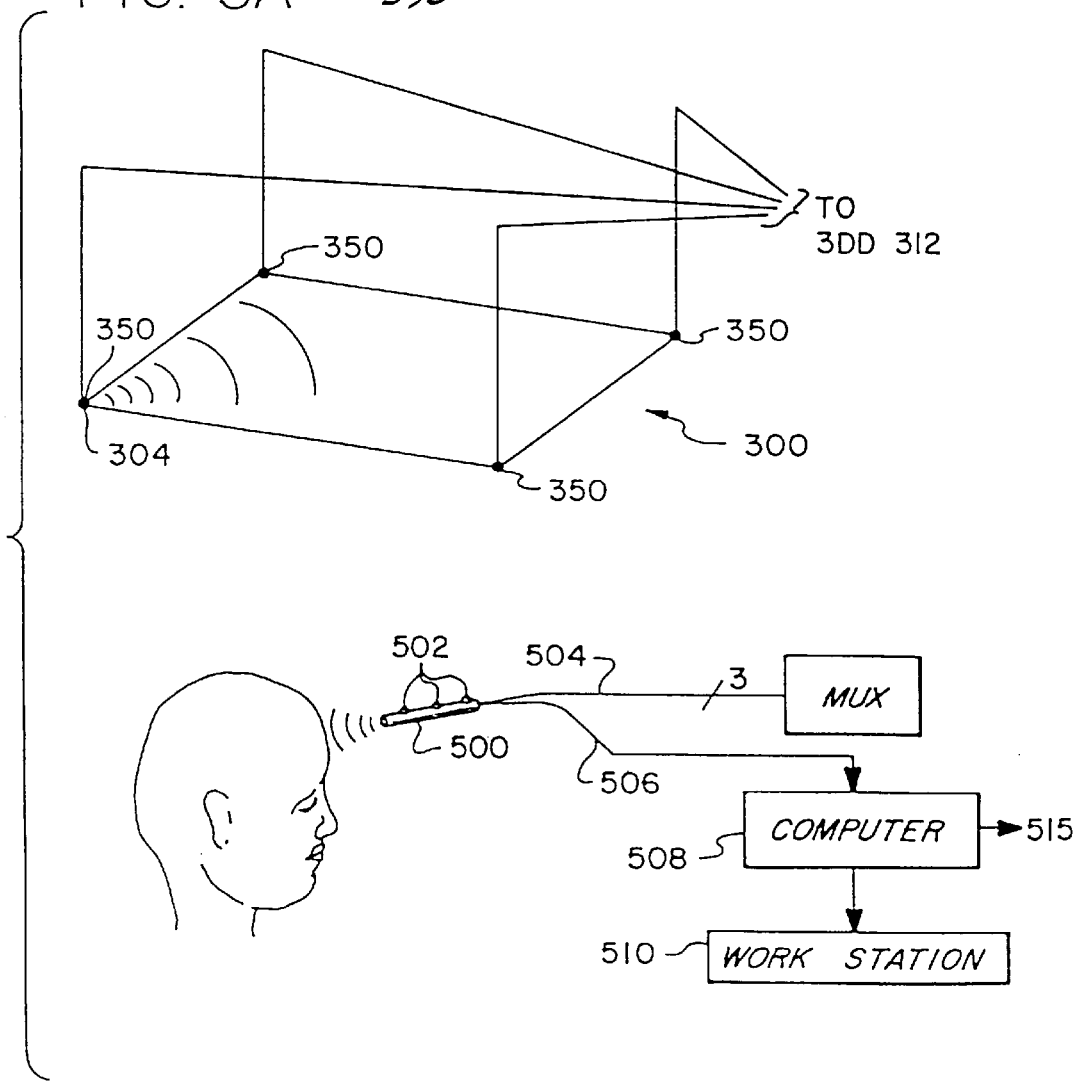
FIG. 5A is a perspective schematic diagram of an ultrasound probe system according to the invention.
Figure 3E:
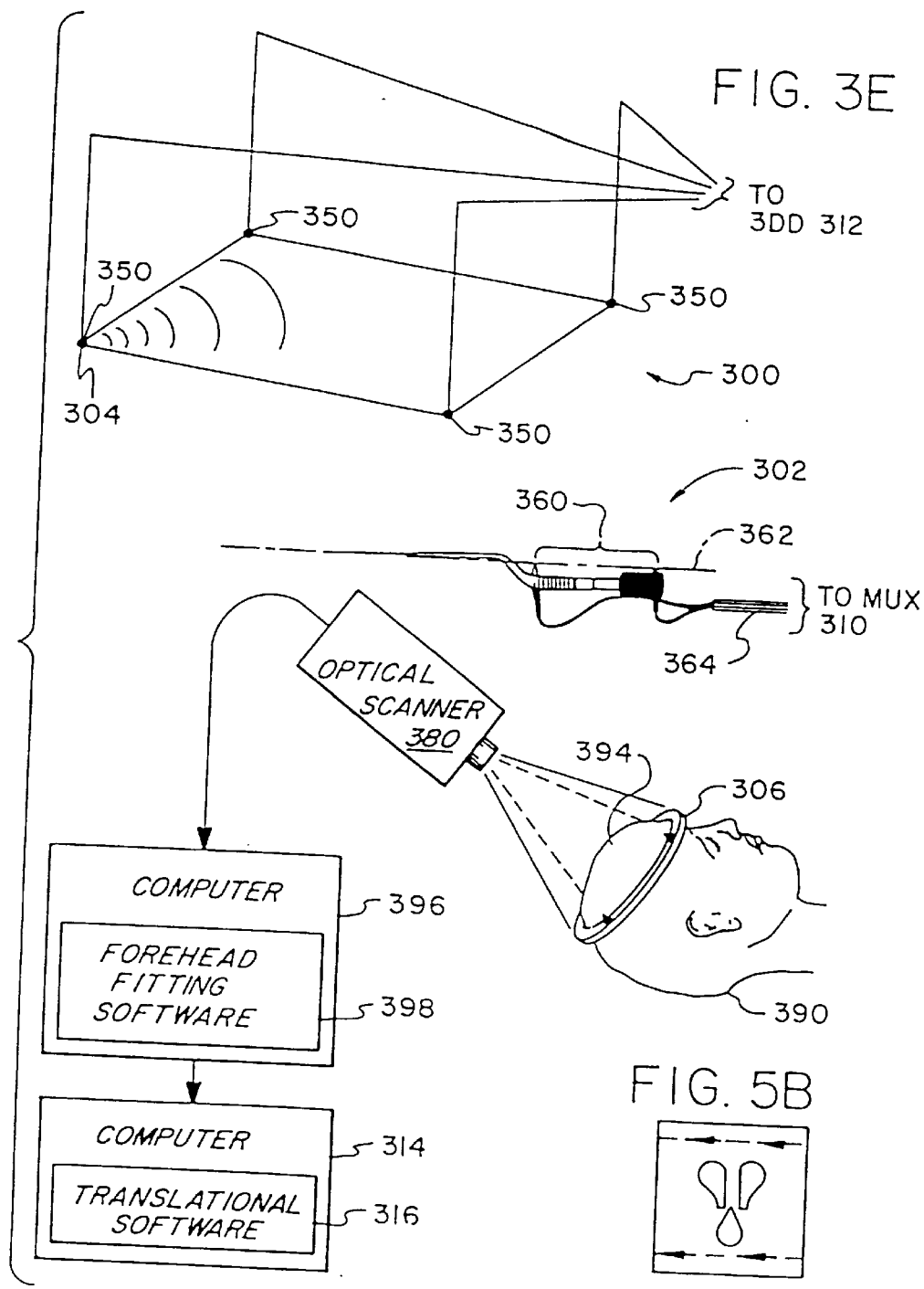
FIG. 3E is a perspective schematic diagram of the microphone array, surgical probe, base ring and optical scanner according to the invention.

Referring to FIG. 5A, a system employing an ultrasound localizer is illustrated. Reference character 500 refers to an ultrasound probe which may be used in the operating room to scan the brain. The ultrasound probe 500 includes a plurality of at least three emitters 502 which communicate with the array 300 to define the plane in which the ultrasound probe is scanning. Emitters 502 are energized via line 504 by multiplexer 310 as in the other systems illustrated above. The radiation emitted by emitters 502 is received by array 300 to determine the plane in which the ultrasound probe 500 is positioned. The ultrasound probe is also connected via line 506 to a computer which analyzes the ultrasound scanning and provides the analyzed information to a work station 510 which displays the scanned image.

Since the array 300 can determine the position of the ultrasound probe 500 at any point in time, via digitizer 312, the particular plane of the image displayed on work station 510 is known. The position of the head of the patient can be determined by attaching a base ring with emitters to the head, as noted above, or by scanning the forehead with an optical scanner having emitters thereon, as noted below.

Figure 5B:
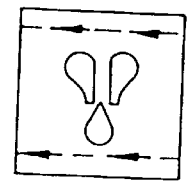
FIGS. 5B and 5C illustrate scanned and ultrasound images, respectively.
Figure 5C:
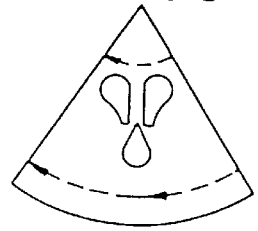

For example, such an ultrasound image is illustrated in FIG. 5C. The surgeon can then call up the similar image on the display 326 of the stereotactic imaging system 324 such as illustrated in FIG. 5B. Alternatively, computer 508 may be linked to the stereotactic imaging system 324 directly to define the particular image plane illustrated on work station 510 so that display 326 can display the corresponding scanned image. As a result, the image from the ultrasound system, as illustrated on work station 510, is shown on one monitor and may be compared to a cross section to the images obtained either by CT, MRI or PET scanning. The cross section through the three dimensional data set as developed by the ultrasound system is determined by a high speed graphics work station, such as manufactured by Silicon Graphics. This allows the interpretation of the ultrasound scans as the anatomy from the MRI, CT or PET scans can be seen directly. Furthermore, the ultrasound system allows scanning in the operating room. Since the brain tissue is elastic and the position of various tissue may change from time to time, use of an ultrasound scan in the operating room permits a more definite localization of various brain tissues.

Alternatively, the system may be used for determining a position of the ultrasound probe relative to a head of a body of a patient. The probe 500 is positioned to scan the head 394 with an array 300 positioned adjacent the probe. At least three emitters 502 permit determination of the position of the ultrasound probe relative to the array. Optical scanner 380, having emitters 381 (FIG. 3D) permit determination of the position of the head relative to the array. Computer 396 translates the position of the ultrasound probe into a coordinate system corresponding to the position of the head.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

I claim:

1. A system for use with a part of a body of a patient, said system comprising:

an ultrasound probe adapted to be positioned adjacent to and scanning the body part;

means, responsive to the ultrasound probe, for generating an ultrasound image of the body part corresponding to the position of the ultrasound probe;

means for determining the position of the ultrasound probe relative to the body part, wherein the determining means comprises:

an array positioned in communication with the ultrasound probe;

first means for determining the position of the ultrasound probe relatively to the array;

second means for determining the position of the body part relative to the array; and means for translating the position of the ultrasound probe as determined by the first means into a coordinate system corresponding to the position of the body part as determined by the second means;

means for scanning the body part to create scanned images thereof; and means, responsive to the scanning means, for generating a scanned image of the body part corresponding to the determined position of the ultrasound probe relative to the body part whereby the ultrasound image of the body part corresponds to and may be compared with the scanned image of the body part.

2. The system of claim 1 wherein the first means comprises at least three emitters on the ultrasound probe and means for activating the emitters to generate a signal communicated to the array.

3. The system of claim 1 wherein the second means comprises means adapted to be mounted on the body part for generating a signal received by the array to indicate the position of the body part relative to the array.

4. A system for use with a part of a body of a patient, said system comprising:

an ultrasound probe adapted to be positioned adjacent to and scanning the body part;

means, responsive to the ultrasound probe, for generating an ultrasound image of the body part corresponding to the position of the ultrasound probe;

means for determining the position of the ultrasound probe relative to the body part, wherein the determining means comprises reference points means having a position in fixed relation to the body part for providing reference points, said scanned images including reference images corresponding to the reference points means;

reference means having a location outside the body part for providing a reference;

first means for determining the position of the ultrasound probe relative to the reference means;

second means for determining the position of the reference points means of the body part relative to the reference means so that the position of the ultrasound probe relative to the reference points means of the body part is a known position; and means for translating the known position of the ultrasound probe to provide a translated position within a coordinate system corresponding to the scanned images of the body part;

means for scanning the body part to create scanned images thereof; and means, responsive to the scanning means, for generating a scanned image of the body part corresponding to the determined position of the ultrasound probe relative to the body part whereby the ultrasound image of the body part corresponds to and may be compared with the scanned image of the body part.

5. The system of claim 4 wherein the second means comprises a base adapted to be mounted on the body part in a position having a fixed relationship with the reference points means of the body and means for measuring the position of the base with respect to the reference means.

6. The system of claim 5 wherein the reference means comprises an array having sensors and wherein the ultrasound probe includes emitters on the probe for communicating with the sensors of the array to indicate a position of the ultrasound probe relative to the array.

7. The system of claim 6 further comprising additional emitters on the base for communicating with the sensors of the array to indicate the position of the base relative to the array.

8. A method for use with a part of the body of a patient, said method comprising the steps of:

scanning the body part with a ultrasound probe positioned adjacent the body part;

generating in response to the scanning step an ultrasound image of the body part corresponding to the position of the ultrasound probe;

determining the position of the ultrasound probe relative to the body part, wherein the determining step comprises the steps of positioning an array in communication with the ultrasound probe;

first determining the position of the ultrasound probe relative to the array;

second determining the position of the body part relative to the array; and translating the position of the ultrasound probe as determined by the first determining step into a coordinate system corresponding to the position of the body part as determined by the second determining step;

scanning the body part to create scanned images thereof; and generating in response to the second scanning step a scanned image of the body part corresponding to the determined position of the ultrasound probe relative to the body part whereby the ultrasound image of the body part corresponds to and may be compared with the scanned image of the body part.

9. The method of claim 8 wherein the first determining step comprises the steps of providing at least three emitters on the ultrasound probe and activating the emitters to generate a signal communicated to the array.

10. The method of claim 8 wherein the second determining step comprises the steps of generating by means on the body part a signal received by the array to indicate the position of the body part relative to the array.

11. A method for use with a part of the body of a patient, said method comprising the steps of:

scanning the body part with an ultrasound probe positioned adjacent the body part;

generating in response to the scanning step an ultrasound image of the body part corresponding to the position of the ultrasound probe;

scanning the body part to create scanned images thereof;

determining the position of the ultrasound probe relative to the body part, wherein the determining step comprises the steps of determining the position of the ultrasound probe relative to a reference means having a position in fixed relation to the body part;

determining the position of the body part relative to the reference means so that the position of the ultrasound probe relative to the body part is a known position; and translating the known position of the ultrasound probe to provide a translated position within a coordinate system corresponding to the scanned images of the body part; and generating in response to the second scanning step a scanned image of the body part corresponding to the determined position of the ultrasound probe relative to the body part whereby the ultrasound image of the body part corresponds to and may be compared with the scanned image of the body part.

12. The method of claim 11 wherein the second determining step comprises the step of mounting a base on the body part in a position having a fixed relationship with the body part and measuring the position of the base with respect to the reference means.

13. The method of claim 12 wherein the reference means comprises an array having sensors and wherein the ultrasound probe includes emitters on the probe for communicating with the sensors of the array to indicate a position of the ultrasound probe relative to the array.

14. A system for providing a display of a scan of a scanning technology, the display showing a cross section of a particular position within the body, said system comprising:

reference points means having a position in relation to the body for providing reference points;

means for generating images of the body, said images including reference images corresponding to the reference points means;

reference means having a position outside the body for providing a reference;

an ultrasound probe having a position and generating an ultrasound image of the body;

first means for determining the position of the ultrasound probe relative to the reference means;

second means for determining the position of the reference points means of the body relative to the reference means so that the position of the ultrasound probe relative to the reference points means of the body is a known position;

means for translating the known position of the ultrasound probe to provide a translated position within a coordinate system corresponding to the images of the body; and means for displaying an image of the body to provide a displayed image which corresponds to the translated position of the ultrasound probe and for displaying the ultrasound image of the body whereby the displayed image and the ultrasound image correspond to each other.

* * * * *

UNITED STATES PATENT AND TRADEMARK OFFICE
CERTIFICATE OF CORRECTION

PATENT NO. : 5,851,183
DATED : December 22, 1998
INVENTOR(S) : Richard D. Bucholz It is certified that error appears in the above-identified patent and that said Letters Patent is hereby corrected as shown below:

On the Title Page, replace the title in entirety with -- System For Use In Displaying Images Of A Body Part--.

On the Title Page, in the related U.S. Application Data, change "May 15, 1992" to -- filed as PCT/US91/07755, October 17, 1991--.

Abstract, 1 should read:

--A system for use in displaying images of a part of a body of a patient includes a probe used to generate an image of the body part corresponding to the position the probe. The position of the probe relative to the body part is determined by determining the position of the probe relative to an array in communication with the probe and determining the position of the body part relative to the array. A scanned image of the body part is also generated corresponding to the determined position of the probe, whereby the various images of the body part may be compared.--

UNITED STATES PATENT AND TRADEMARK OFFICE
CERTIFICATE OF CORRECTION

PATENT NO. : 5,851,183
DATED : December 22, 1998
INVENTOR(S) : Richard D. Bucholz It is certified that error appears in the above-identified patent and that said Letters Patent is hereby corrected as shown below:

In Col. 1, line 6, change "filed on May 15, 1992" to -- which was the National Stage of International Application No. PCT/US91/07755, filed October 17, 1991 --;

In Claim 1, Col. 13, line 48, change "with" to --in displaying images of --;
        line 61, change "relatively" to --relative--.

In Claim 4, Col. 14, line 17, change "with" to --in displaying images of --;

In Claim 8, Col. 14, line 66, change "with" to --in displaying images of --;

In Claim 11, Col. 15, line 37, change "with" to --in displaying images of --.

Signed and Sealed this

Twenty-fifth Day of May, 1999

*Attest:*

*Attesting Officer*

Q. TODD DICKINSON

*Acting Commissioner of Patents and Trademarks*